(12) United States Patent
Peters et al.

(10) Patent No.: US 7,674,958 B2
(45) Date of Patent: Mar. 9, 2010

(54) GRG23 AND GRG51 GENES CONFERRING HERBICIDE RESISTANCE

(75) Inventors: Cheryl L. Peters, Raleigh, NC (US); Jill Hinson, Rougemont, NC (US); Philip E. Hammer, Cary, NC (US); Brian Vande Berg, Durham, NC (US); Laura Cooper Schouten, Sanford, NC (US); Brian Carr, Raleigh, NC (US)

(73) Assignee: Athenix Corporation, Research Triangle Park, NC (US)

( * ) Notice: Subject to any disclaimer, the term of this patent is extended or adjusted under 35 U.S.C. 154(b) by 481 days.

(21) Appl. No.: 11/605,824

(22) Filed: Nov. 29, 2006

(65) Prior Publication Data

US 2007/0136840 A1    Jun. 14, 2007

Related U.S. Application Data

(60) Provisional application No. 60/741,166, filed on Dec. 1, 2005, provisional application No. 60/817,799, filed on Jun. 30, 2006.

(51) Int. Cl.
*C12N 15/82* (2006.01)
*C12N 15/63* (2006.01)
*C12N 15/52* (2006.01)

(52) U.S. Cl. ............. 800/300; 435/252.3; 435/320.1; 435/419; 536/23.2; 800/288; 800/300.1

(58) Field of Classification Search .............. None
See application file for complete search history.

(56) References Cited

U.S. PATENT DOCUMENTS 5,633,435 A * 5/1997 Barry et al. .............. 800/288
2006/0143727 A1   6/2006 Alibhai et al.

OTHER PUBLICATIONS

Vazquez, M.A., et al., "Determination of Phosphate in Nanomolar Range by an Enzyme-coupling Fluorescent Method," *Analytical Biochemistry*, 2003, pp. 292-298, vol. 320.

NCBI Database Accession No. YP-174720, direct submission on Jan. 3, 2005.

NCBI Database Accession No. YP-644215, direct submission on Jun. 12, 2006.

Padgette, S.R., et al., "Site-directed Mutagenesis of a Conserved Region of the 5-Enolpyruvylshikimate-3-phosphate Synthase Active Site," *J. Biol. Chem.*, Nov. 25, 1991, pp. 22364-22368, vol. 266, No. 33.

Pipke, R. and N. Amrhein, "Degradation of the Phosphonate Herbicide Glyphosate by *Arthrobacter atrocyaneus* ATCC 13752," *Applied and Environmental Microbiology*, May 1988, pp. 1293-1296, vol. 54, No. 5.

Pipke, R. and N. Amrhein, "Isolation and Characterization of a Mutant of *Arthrobacter* sp. Strain GLP-1 Which Utilizes the Herbicide Glyphosate as Its Sole Source of Phosphorus and Nitrogen," *Applied and Environmental Microbiology*, Nov. 1988, pp. 2868-2870, vol. 54, No. 11.

* cited by examiner

*Primary Examiner*—David H Kruse
(74) *Attorney, Agent, or Firm*—Alston & Bird LLP

(57) ABSTRACT

Compositions and methods for conferring herbicide resistance or tolerance to bacteria, plants, plant cells, tissues and seeds are provided. Compositions include polynucleotides encoding herbicide resistance or tolerance polypeptides, vectors comprising those polynucleotides, and host cells comprising the vectors. The nucleotide sequences of the invention can be used in DNA constructs or expression cassettes for transformation and expression in organisms, including microorganisms and plants. Compositions also comprise transformed bacteria, plants, plant cells, tissues, and seeds. In particular, isolated polynucleotides encoding glyphosate resistance or tolerance polypeptides are provided. Additionally, amino acid sequences corresponding to the polynucleotides are encompassed. In particular, the present invention provides for isolated polynucleotides comprising nucleotide sequences encoding the amino acid sequence shown in SEQ ID NO:2, 4, or 6, or the nucleotide sequence set forth in SEQ ID NO:1, 3, or 5. The present invention additionally provides a method to measure enzyme kinetic activity using fluorogenic substrates.

13 Claims, 5 Drawing Sheets

```
                   *         380         *         400         *         420
GRG23          : TLAATABLADGBITITNIGHARLKESDRISAMETNLRTLEVQTDVGHDMMRIYPS----- :  375
GRG51          : TLAATABLADGBITITNIGHARLKESDRISAMESNLRMLGVQTDVGHDMMRIYPS----- :  352
B_Clausii      : TLAATSPEADGEAIEGVGHIRHECDRIRAICEETSRLGTRVEERHDGITWYEG------- :  386
R_xylanophilus : TLAAPEASSETLIKNVAETRIQETDRLAAAELSRLGTRVRMHETPDSLRIIEG------- :  392
E_coli         : TIATABAKCTRLRNIYNMRVKETDRLEAMATELRKVGAEVEGHDYMIRITPP-------- :  371
CP4            : ILAVAAAEAPVMNGLEELRVKESDRLSAVANGIKLNEVDCDEGETSLVVRGRPDGKG--- :  389
Zea_maize      : TLAVALEDGTAIRDVASWRVKETERMVAIREELTKLGASVEEGPDYCIITPp-------- :  389
                 t6A    a  A  g       6         R   E  dR6 A6      L   G      d   6 p

*         440         *         460         *         480
GRG23          : ---TPHGGRVNCHRDHRIAMAESILGLRVDG-IELDDPQCVGKTEPGFEDYLGRIFPEKA :  431
GRG51          : ---TPHGGRVNCHRDHRIAMAESILGLRVDG-IELDDPQCVGKTEPGFEDYLGRIFPEKA :  408
B_Clausii      : ---QPKPTVNIDDHRMAMANALALICAWDG--IELDDGCVAKTCPSYESMLAQTGIGVK- :  442
R_xylanophilus : ---KVRPAAIRTYGDHRMAMAFSLVGLRVRG-VRILDPGYRLEGLRRGG----------- :  447
E_coli         : --EKLNFAEIAIYNDHRMANCFSVAISDTP--VEILDEKTARTEPDYEEQLARISQAA-- :  427
CP4            : LG-NASGAAVATHLDHRIANSELVMGLVSENPVDATMIATSPEMDLMAGTGAKIE----- :  448
Zea_maize      : --EKLNVTAIDYDDHRMAMAESLAACAEVP--VEIRDGCTRKTEDYEDVLSTFVKN---- :  444
                         DHR6AM f 6            6  6 Dp  c   k3 p 5f  6

GRG23          : LTLPG-- :  436
GRG51          : LTLPG-- :  413
B_Clausii      : AVSP--- :  446
R_xylanophilus : ------- :    -
E_coli         : ------- :    -
CP4            : LSDTKAA :  455
Zea_maize      : ------- :    -
```

FIG. 1C

SEQUENCE LISTING

<160> NUMBER OF SEQ ID NOS: 36

<210> SEQ ID NO 1
<211> LENGTH: 1892
<212> TYPE: DNA
<213> ORGANISM: Arthrobacter globiformis
<220> FEATURE:
<221> NAME/KEY: misc_feature
<222> LOCATION: (0)...(0)
<223> OTHER INFORMATION: Strain ATX21308
<221> NAME/KEY: CDS

```
<222> LOCATION: (109)...(1419)
<221> NAME/KEY: misc_feature
<222> LOCATION: 1801
<223> OTHER INFORMATION: n = A,T,C or G
<221> NAME/KEY: misc_feature
<222> LOCATION: 1801
<223> OTHER INFORMATION: n = A,T,C or G

<400> SEQUENCE: 1
gggaccacat gctgctcctg atttcagggc tgctgccggt atggaccagg gtttagagag      60
ggacggcacg catccgggcc cttatcggac caacgccaac agcggtcg gtg gcc ttg     117
                                                    Met Ala Leu
                                                      1 gag cgg ggc cag cac ggc cga tca cgt aga ctc ttt gga gct tcg ctc      165
Glu Arg Gly Gln His Gly Arg Ser Arg Arg Leu Phe Gly Ala Ser Leu
  5                  10                  15 gaa agg atc acc atg gaa act gat cga cta gtg atc cca gga tcg aaa      213
Glu Arg Ile Thr Met Glu Thr Asp Arg Leu Val Ile Pro Gly Ser Lys
 20                  25                  30                  35 agc atc acc aac cgg gct ttg ctt ttg gct gcc gca gcg aag ggc acg      261
Ser Ile Thr Asn Arg Ala Leu Leu Leu Ala Ala Ala Lys Gly Thr
             40                  45                  50 tcg gtc ctg gtg aga cca ttg gtc agc gcc gat acc tca gca ttc aaa      309
Ser Val Leu Val Arg Pro Leu Val Ser Ala Asp Thr Ser Ala Phe Lys
         55                  60                  65 act gca att cag gcc ctc ggt gcc aac gtc tca gcc gac ggt gac aat      357
Thr Ala Ile Gln Ala Leu Gly Ala Asn Val Ser Ala Asp Gly Asp Asn
     70                  75                  80 tgg gtc gtt gaa ggc ctg ggt cag gca ccc cac ctc gac gcc gac atc      405
Trp Val Val Glu Gly Leu Gly Gln Ala Pro His Leu Asp Ala Asp Ile
 85                  90                  95 tgg tgc gag gat gca ggt acc gtg gcc cgg ttc ctc cct cca ttc gtc      453
Trp Cys Glu Asp Ala Gly Thr Val Ala Arg Phe Leu Pro Pro Phe Val
100                 105                 110                 115 gcc gca gga cag ggg aag ttc acc gtc gac gga agc gag cag ctg cgg      501
Ala Ala Gly Gln Gly Lys Phe Thr Val Asp Gly Ser Glu Gln Leu Arg
                 120                 125                 130 cgg cgc ccg ctt cgg ccc ctg gtc gac ggc atc cgc cac ctg ggc gcc      549
Arg Arg Pro Leu Arg Pro Leu Val Asp Gly Ile Arg His Leu Gly Ala
             135                 140                 145 cgc gtc tcc tcc gag cag ctg ccc cta aca att gaa gcg agc ggg ctg      597
Arg Val Ser Ser Glu Gln Leu Pro Leu Thr Ile Glu Ala Ser Gly Leu
         150                 155                 160 gca ggc ggg gag tac gaa att gaa gcc cat cag agc agc cag ttc gcc      645
Ala Gly Gly Glu Tyr Glu Ile Glu Ala His Gln Ser Ser Gln Phe Ala
165                 170                 175 tcc ggc ctg atc atg gcc gcc ccg tac gcg cga caa ggc ctg cgt gtg      693
Ser Gly Leu Ile Met Ala Ala Pro Tyr Ala Arg Gln Gly Leu Arg Val
180                 185                 190                 195 cgg ata cca aat ccc gtg agc cag ccc tac ctc acg atg aca ctg cgg      741
Arg Ile Pro Asn Pro Val Ser Gln Pro Tyr Leu Thr Met Thr Leu Arg
                 200                 205                 210 atg atg agg gac ttc ggc ctt gag acc agc acc gac gga gcc acc gtc      789
Met Met Arg Asp Phe Gly Leu Glu Thr Ser Thr Asp Gly Ala Thr Val
             215                 220                 225 agc gtc cct ccc ggg cgc tac aca gcc cgg cgg tat gaa att gaa ccg      837
Ser Val Pro Pro Gly Arg Tyr Thr Ala Arg Arg Tyr Glu Ile Glu Pro
         230                 235                 240 gac gcg tca act gcg tcg tac ttc gcc gcc gct tcc gcc gtc tct ggc      885
Asp Ala Ser Thr Ala Ser Tyr Phe Ala Ala Ala Ser Ala Val Ser Gly
245                 250                 255
```

```
cga agc ttc gaa ttc cag ggc ctt ggc aca gac agc atc caa ggc gac      933
Arg Ser Phe Glu Phe Gln Gly Leu Gly Thr Asp Ser Ile Gln Gly Asp
260                 265                 270                 275 acg tca ttc ttc aat gta ctt ggg cgg ctc ggt gca gag gtc cac tgg      981
Thr Ser Phe Phe Asn Val Leu Gly Arg Leu Gly Ala Glu Val His Trp
                280                 285                 290 gca ccc aac tcg gtc acc ata tcc gga ccg gaa agg ctg aac ggc gac     1029
Ala Pro Asn Ser Val Thr Ile Ser Gly Pro Glu Arg Leu Asn Gly Asp
            295                 300                 305 att gaa gtg gat atg ggc gag ata tcg gac acc ttc atg aca ctc gcg     1077
Ile Glu Val Asp Met Gly Glu Ile Ser Asp Thr Phe Met Thr Leu Ala
        310                 315                 320 gcg att gcc cct cta gcc gat gga ccc atc acg ata acc aac att ggc     1125
Ala Ile Ala Pro Leu Ala Asp Gly Pro Ile Thr Ile Thr Asn Ile Gly
    325                 330                 335 cat gca cgg ttg aag gaa tcc gac cgc atc tcg gcg atg gaa acc aac     1173
His Ala Arg Leu Lys Glu Ser Asp Arg Ile Ser Ala Met Glu Thr Asn
340                 345                 350                 355 ctg cga acg ctc ggt gta caa acc gac gtc gga cac gac tgg atg cga     1221
Leu Arg Thr Leu Gly Val Gln Thr Asp Val Gly His Asp Trp Met Arg
                360                 365                 370 atc tac ccc tct acc ccg cac ggc ggc aga gtc aat tgc cac cgg gac     1269
Ile Tyr Pro Ser Thr Pro His Gly Gly Arg Val Asn Cys His Arg Asp
            375                 380                 385 cac agg atc gcc atg gcg ttt tca atc ctg gga ctg cga gtg gac ggg     1317
His Arg Ile Ala Met Ala Phe Ser Ile Leu Gly Leu Arg Val Asp Gly
        390                 395                 400 att acc ctc gac gac cct caa tgt gtc ggg aag acc ttt cct ggc ttc     1365
Ile Thr Leu Asp Asp Pro Gln Cys Val Gly Lys Thr Phe Pro Gly Phe
    405                 410                 415 ttc gac tac ctt gga cgc ctt ttc ccc gaa aag gcg ctt acg ctc ccc     1413
Phe Asp Tyr Leu Gly Arg Leu Phe Pro Glu Lys Ala Leu Thr Leu Pro
420                 425                 430                 435 ggc tag tgacttcctc tccggcggac gctaggcatc ggaaaacgaa tcctgacatg     1469
Gly * accgacctcc tcgcgtcacg gcgtgtctgc cggtacccaa gcattctgcc ttagccgctt     1529
ccgcggcccc ttatgctttc tggttgtcca gattttcatc cgggatgttg cctgaccttg     1589
agcagggcaa tcagctgttc agcactgtca atggtgtggg ccctgaaggc ggcttcgatg     1649
gctgccacgt cggcggctct catcgctgtc acgacacgca gatgcgcttc ataggcacgt     1709
tcaggatccg ccctcgtcgc ctgatcctga gccaaggcaa tagttagatg tgcctccgtt     1769
ggcggccaga gccgaagcaa taaggagttt tncgaggcca cccagattcc ccgggtggaa     1829
ggcgatatgg gcttcatgct gaactatggg gtccggatgg aagtgacttt tcaactctgc     1889
cca                                                                  1892

<210> SEQ ID NO 2
<211> LENGTH: 436
<212> TYPE: PRT
<213> ORGANISM: Arthrobacter globiformis

<400> SEQUENCE: 2

Met Ala Leu Glu Arg Gly Gln His Gly Arg Ser Arg Arg Leu Phe Gly
1               5                   10                  15

Ala Ser Leu Glu Arg Ile Thr Met Glu Thr Asp Arg Leu Val Ile Pro
            20                  25                  30

Gly Ser Lys Ser Ile Thr Asn Arg Ala Leu Leu Leu Ala Ala Ala Ala
```

```
                    35                  40                  45
Lys Gly Thr Ser Val Leu Val Arg Pro Leu Val Ser Ala Asp Thr Ser
         50                  55                  60

Ala Phe Lys Thr Ala Ile Gln Ala Leu Gly Ala Asn Val Ser Ala Asp
 65                  70                  75                  80

Gly Asp Asn Trp Val Val Glu Gly Leu Gly Gln Ala Pro His Leu Asp
                 85                  90                  95

Ala Asp Ile Trp Cys Glu Asp Ala Gly Thr Val Ala Arg Phe Leu Pro
            100                 105                 110

Pro Phe Val Ala Ala Gly Gln Gly Lys Phe Thr Val Asp Gly Ser Glu
            115                 120                 125

Gln Leu Arg Arg Arg Pro Leu Arg Pro Leu Val Asp Gly Ile Arg His
        130                 135                 140

Leu Gly Ala Arg Val Ser Ser Glu Gln Leu Pro Leu Thr Ile Glu Ala
145                 150                 155                 160

Ser Gly Leu Ala Gly Gly Glu Tyr Glu Ile Glu Ala His Gln Ser Ser
                165                 170                 175

Gln Phe Ala Ser Gly Leu Ile Met Ala Ala Pro Tyr Ala Arg Gln Gly
            180                 185                 190

Leu Arg Val Arg Ile Pro Asn Pro Val Ser Gln Pro Tyr Leu Thr Met
        195                 200                 205

Thr Leu Arg Met Met Arg Asp Phe Gly Leu Glu Thr Ser Thr Asp Gly
        210                 215                 220

Ala Thr Val Ser Val Pro Pro Gly Arg Tyr Thr Ala Arg Arg Tyr Glu
225                 230                 235                 240

Ile Glu Pro Asp Ala Ser Thr Ala Ser Tyr Phe Ala Ala Ala Ser Ala
                245                 250                 255

Val Ser Gly Arg Ser Phe Glu Phe Gln Gly Leu Gly Thr Asp Ser Ile
            260                 265                 270

Gln Gly Asp Thr Ser Phe Phe Asn Val Leu Gly Arg Leu Gly Ala Glu
            275                 280                 285

Val His Trp Ala Pro Asn Ser Val Thr Ile Ser Gly Pro Glu Arg Leu
        290                 295                 300

Asn Gly Asp Ile Glu Val Asp Met Gly Glu Ile Ser Asp Thr Phe Met
305                 310                 315                 320

Thr Leu Ala Ala Ile Ala Pro Leu Ala Asp Gly Pro Ile Thr Ile Thr
                325                 330                 335

Asn Ile Gly His Ala Arg Leu Lys Glu Ser Asp Arg Ile Ser Ala Met
            340                 345                 350

Glu Thr Asn Leu Arg Thr Leu Gly Val Gln Thr Asp Val Gly His Asp
        355                 360                 365

Trp Met Arg Ile Tyr Pro Ser Thr Pro His Gly Gly Arg Val Asn Cys
    370                 375                 380

His Arg Asp His Arg Ile Ala Met Ala Phe Ser Ile Leu Gly Leu Arg
385                 390                 395                 400

Val Asp Gly Ile Thr Leu Asp Asp Pro Gln Cys Val Gly Lys Thr Phe
                405                 410                 415

Pro Gly Phe Phe Asp Tyr Leu Gly Arg Leu Phe Pro Glu Lys Ala Leu
            420                 425                 430

Thr Leu Pro Gly
        435

<210> SEQ ID NO 3
```

```
<211> LENGTH: 1892
<212> TYPE: DNA
<213> ORGANISM: Arthrobacter globiformis
<220> FEATURE:
<221> NAME/KEY: CDS
<222> LOCATION: (178)...(1419)
<221> NAME/KEY: misc_feature
<222> LOCATION: 1801
<223> OTHER INFORMATION: n = A,T,C or G

<400> SEQUENCE: 3
```

| | | |
|---|---|---|
| gggaccacat gctgctcctg atttcagggc tgctgccggt atggaccagg gtttagagag | | 60 |
| ggacggcacg catccgggcc cttatcggac caacgccaac agcggtcggt ggccttggag | | 120 |
| cggggccagc acggccgatc acgtagactc tttggagctt cgctcgaaag gatcacc atg<br>                                                                                                          Met<br>                                                                                                            1 | | 180 |

```
gaa act gat cga cta gtg atc cca gga tcg aaa agc atc acc aac cgg       228
Glu Thr Asp Arg Leu Val Ile Pro Gly Ser Lys Ser Ile Thr Asn Arg
         5                  10                  15 gct ttg ctt ttg gct gcc gca gcg aag ggc acg tcg gtc ctg gtg aga       276
Ala Leu Leu Leu Ala Ala Ala Ala Lys Gly Thr Ser Val Leu Val Arg
     20                  25                  30 cca ttg gtc agc gcc gat acc tca gca ttc aaa act gca att cag gcc       324
Pro Leu Val Ser Ala Asp Thr Ser Ala Phe Lys Thr Ala Ile Gln Ala
 35                  40                  45 ctc ggt gcc aac gtc tca gcc gac ggt gac aat tgg gtc gtt gaa ggc       372
Leu Gly Ala Asn Val Ser Ala Asp Gly Asp Asn Trp Val Val Glu Gly
 50                  55                  60                  65 ctg ggt cag gca ccc cac ctc gac gcc gac atc tgg tgc gag gat gca       420
Leu Gly Gln Ala Pro His Leu Asp Ala Asp Ile Trp Cys Glu Asp Ala
             70                  75                  80 ggt acc gtg gcc cgg ttc ctc cct cca ttc gtc gcc gca gga cag ggg       468
Gly Thr Val Ala Arg Phe Leu Pro Pro Phe Val Ala Ala Gly Gln Gly
         85                  90                  95 aag ttc acc gtc gac gga agc gag cag ctg cgg cgg cgc ccg ctt cgg       516
Lys Phe Thr Val Asp Gly Ser Glu Gln Leu Arg Arg Arg Pro Leu Arg
    100                 105                 110 ccc ctg gtc gac ggc atc cgc cac ctg ggc gcc cgc gtc tcc tcc gag       564
Pro Leu Val Asp Gly Ile Arg His Leu Gly Ala Arg Val Ser Ser Glu
115                 120                 125 cag ctg ccc cta aca att gaa gcg agc ggg ctg gca ggc ggg gag tac       612
Gln Leu Pro Leu Thr Ile Glu Ala Ser Gly Leu Ala Gly Gly Glu Tyr
130                 135                 140                 145 gaa att gaa gcc cat cag agc agc cag ttc gcc tcc ggc ctg atc atg       660
Glu Ile Glu Ala His Gln Ser Ser Gln Phe Ala Ser Gly Leu Ile Met
                150                 155                 160 gcc gcc ccg tac gcg cga caa ggc ctg cgt gtg cgg ata cca aat ccc       708
Ala Ala Pro Tyr Ala Arg Gln Gly Leu Arg Val Arg Ile Pro Asn Pro
            165                 170                 175 gtg agc cag ccc tac ctc acg atg aca ctg cgg atg atg agg gac ttc       756
Val Ser Gln Pro Tyr Leu Thr Met Thr Leu Arg Met Met Arg Asp Phe
        180                 185                 190 ggc ctt gag acc agc acc gac gga gcc acc gtc agc gtc cct ccc ggg       804
Gly Leu Glu Thr Ser Thr Asp Gly Ala Thr Val Ser Val Pro Pro Gly
    195                 200                 205 cgc tac aca gcc cgg cgg tat gaa att gaa ccg gac gcg tca act gcg       852
Arg Tyr Thr Ala Arg Arg Tyr Glu Ile Glu Pro Asp Ala Ser Thr Ala
210                 215                 220                 225 tcg tac ttc gcc gcc gct tcc gcc gtc tct ggc gga agc ttc gaa ttc       900
Ser Tyr Phe Ala Ala Ala Ser Ala Val Ser Gly Arg Ser Phe Glu Phe
                230                 235                 240
```

```
cag ggc ctt ggc aca gac agc atc caa ggc gac acg tca ttc ttc aat      948
Gln Gly Leu Gly Thr Asp Ser Ile Gln Gly Asp Thr Ser Phe Phe Asn
            245                 250                 255 gta ctt ggg cgg ctc ggt gca gag gtc cac tgg gca ccc aac tcg gtc      996
Val Leu Gly Arg Leu Gly Ala Glu Val His Trp Ala Pro Asn Ser Val
        260                 265                 270 acc ata tcc gga ccg gaa agg ctg aac ggc gac att gaa gtg gat atg     1044
Thr Ile Ser Gly Pro Glu Arg Leu Asn Gly Asp Ile Glu Val Asp Met
    275                 280                 285 ggc gag ata tcg gac acc ttc atg aca ctc gcg gcg att gcc cct cta     1092
Gly Glu Ile Ser Asp Thr Phe Met Thr Leu Ala Ala Ile Ala Pro Leu
290                 295                 300                 305 gcc gat gga ccc atc acg ata acc aac att ggc cat gca cgg ttg aag     1140
Ala Asp Gly Pro Ile Thr Ile Thr Asn Ile Gly His Ala Arg Leu Lys
            310                 315                 320 gaa tcc gac cgc atc tcg gcg atg gaa acc aac ctg cga acg ctc ggt     1188
Glu Ser Asp Arg Ile Ser Ala Met Glu Thr Asn Leu Arg Thr Leu Gly
        325                 330                 335 gta caa acc gac gtc gga cac gac tgg atg cga atc tac ccc tct acc     1236
Val Gln Thr Asp Val Gly His Asp Trp Met Arg Ile Tyr Pro Ser Thr
    340                 345                 350 ccg cac ggc ggc aga gtc aat tgc cac cgg gac cac agg atc gcc atg     1284
Pro His Gly Gly Arg Val Asn Cys His Arg Asp His Arg Ile Ala Met
355                 360                 365 gcg ttt tca atc ctg gga ctg cga gtg gac ggg att acc ctc gac gac     1332
Ala Phe Ser Ile Leu Gly Leu Arg Val Asp Gly Ile Thr Leu Asp Asp
370                 375                 380                 385 cct caa tgt gtc ggg aag acc ttt cct ggc ttc ttc gac tac ctt gga     1380
Pro Gln Cys Val Gly Lys Thr Phe Pro Gly Phe Phe Asp Tyr Leu Gly
            390                 395                 400 cgc ctt ttc ccc gaa aag gcg ctt acg ctc ccc ggc tag tgacttcctc      1429
Arg Leu Phe Pro Glu Lys Ala Leu Thr Leu Pro Gly  *
        405                 410 tccggcggac gctaggcatc ggaaaacgaa tcctgacatg accgacctcc tcgcgtcacg   1489
gcgtgtctgc cggtacccaa gcattctgcc ttagccgctt ccgcggcccc ttatgctttc   1549
tggttgtcca gattttcatc cgggatgttg cctgaccttg agcagggcaa tcagctgttc   1609
agcactgtca atggtgtggg ccctgaaggc ggcttcgatg gctgccacgt cggcggctct   1669
catcgctgtc acgacacgca gatgcgcttc ataggcacgt tcaggatccg ccctcgtcgc   1729
ctgatcctga gccaaggcaa tagttagatg tgcctccgtt ggcggccaga gccgaagcaa   1789
taaggagttt tncgaggcca cccagattcc ccgggtggaa ggcgatatgg gcttcatgct   1849
gaactatggg gtccggatgg aagtgacttt tcaactctgc cca                    1892

<210> SEQ ID NO 4
<211> LENGTH: 413
<212> TYPE: PRT
<213> ORGANISM: Arthrobacter globiformis

<400> SEQUENCE: 4

Met Glu Thr Asp Arg Leu Val Ile Pro Gly Ser Lys Ser Ile Thr Asn
 1               5                  10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
```

```
                50                  55                  60
Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Asp Thr Ser Phe Phe
                245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 5
<211> LENGTH: 1242
<212> TYPE: DNA
<213> ORGANISM: Unknown
<220> FEATURE:
<223> OTHER INFORMATION: Isolated from soil sample
<221> NAME/KEY: CDS
<222> LOCATION: (1)...(1242)

<400> SEQUENCE: 5
```

```
atg gaa act gat cga cta gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc gcg tcg gtc ctg gtg      96
Arg Ala Leu Leu Leu Ala Ala Ala Ala Lys Gly Ala Ser Val Leu Val
                20                  25                  30 aga cca ttg gtc agc gcc gat acc tca gca ttc aaa act gca att cag     144
Arg Pro Leu Val Ser Ala Asp Thr Ser Ala Phe Lys Thr Ala Ile Gln
            35                  40                  45 gcc ctc ggt gcc aac gtc tca gcg gac ggt gat gat tgg gtc gtt gaa     192
Ala Leu Gly Ala Asn Val Ser Ala Asp Gly Asp Asp Trp Val Val Glu
 50                  55                  60 ggc ctg ggc cag gca ccc aac ctc gac gcc gac atc tgg tgc gag gat     240
Gly Leu Gly Gln Ala Pro Asn Leu Asp Ala Asp Ile Trp Cys Glu Asp
 65                  70                  75                  80 gcc ggt acc gtg gcc cgg ttc ctc cct cca ttc gtc gcc gca gga cag     288
Ala Gly Thr Val Ala Arg Phe Leu Pro Pro Phe Val Ala Ala Gly Gln
                85                  90                  95 ggg aag ttc acc gtc gac gga agc gag cag ctg cgg cgg cgc ccg ctt     336
Gly Lys Phe Thr Val Asp Gly Ser Glu Gln Leu Arg Arg Arg Pro Leu
            100                 105                 110 cgg ccc gtg gtc gac ggc atc cgc cac ctg ggc gcc cgc gtc tcc tcc     384
Arg Pro Val Val Asp Gly Ile Arg His Leu Gly Ala Arg Val Ser Ser
        115                 120                 125 gag cag ctg ccc cta acg att gaa gcg agc ggg ctg gca ggc ggg gag     432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggt ctg atc     480
Tyr Glu Ile Glu Ala His Gln Ser Ser Gln Phe Ala Ser Gly Leu Ile
145                 150                 155                 160 atg gcc gcc ccg tac gcg cga caa ggc ctg cgt gtt cgg ata cca aat     528
Met Ala Ala Pro Tyr Ala Arg Gln Gly Leu Arg Val Arg Ile Pro Asn
                165                 170                 175 ccc gtg agc cag ccc tac ctc acg atg aca ctg cgg atg atg agg gac     576
Pro Val Ser Gln Pro Tyr Leu Thr Met Thr Leu Arg Met Met Arg Asp
            180                 185                 190 ttc ggc att gag acc agc acc gac gga gcg acc gtc agc gtt cct ccc     624
Phe Gly Ile Glu Thr Ser Thr Asp Gly Ala Thr Val Ser Val Pro Pro
        195                 200                 205 ggg cgc tac aca gcg cgg cgg tat gag att gaa ccg gac gcg tca act     672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc cgg cgc ttc gaa     720
Ala Ser Tyr Phe Ala Ala Ala Ser Ala Val Ser Gly Arg Arg Phe Glu
225                 230                 235                 240 ttc cag ggc ctt ggc aca gac agc atc caa ggc gac acg tca ttc ttc     768
Phe Gln Gly Leu Gly Thr Asp Ser Ile Gln Gly Asp Thr Ser Phe Phe
                245                 250                 255 aat gta ctt ggg cgg ctc ggc gca gag gtc cac tgg gca tcc aac tcg     816
Asn Val Leu Gly Arg Leu Gly Ala Glu Val His Trp Ala Ser Asn Ser
            260                 265                 270 gtc acc ata tcc gga ccg gaa agg ctg acc ggc gac att gaa gtg gat     864
Val Thr Ile Ser Gly Pro Glu Arg Leu Thr Gly Asp Ile Glu Val Asp
        275                 280                 285 atg ggc gag ata tcg gac acc ttc atg aca ctg gcg gcg att gcc cct     912
Met Gly Glu Ile Ser Asp Thr Phe Met Thr Leu Ala Ala Ile Ala Pro
    290                 295                 300 cta gcc gat gga ccc atc acg ata aca aac att ggc cat gca cgg ttg     960
Leu Ala Asp Gly Pro Ile Thr Ile Thr Asn Ile Gly His Ala Arg Leu
```

```
                305                 310                 315                 320
aag gaa tcc gac cgc atc tcg gcg atg gaa agc aac ctt cga atg ctc         1008
Lys Glu Ser Asp Arg Ile Ser Ala Met Glu Ser Asn Leu Arg Met Leu
                325                 330                 335 ggt gta caa acc gac gtc gga cac gac tgg atg cga atc tac ccc tct         1056
Gly Val Gln Thr Asp Val Gly His Asp Trp Met Arg Ile Tyr Pro Ser
            340                 345                 350 acc ccg cac ggc ggc aga gtc aat tgc cac cgg gac cac agg atc gcc         1104
Thr Pro His Gly Gly Arg Val Asn Cys His Arg Asp His Arg Ile Ala
            355                 360                 365 atg gcg ttt tca atc ctg gga ctg cga gtg gac ggg att acc ctc gac         1152
Met Ala Phe Ser Ile Leu Gly Leu Arg Val Asp Gly Ile Thr Leu Asp
        370                 375                 380 gac cct caa tgt gtc ggg aag acc ttt cct ggc ttc ttc gac tac ctt         1200
Asp Pro Gln Cys Val Gly Lys Thr Phe Pro Gly Phe Phe Asp Tyr Leu
385                 390                 395                 400 gga cgc ctt ttc ccg gaa aag gcg ctt acg ctc ccc ggc tag             1242
Gly Arg Leu Phe Pro Glu Lys Ala Leu Thr Leu Pro Gly  *
                405                 410

<210> SEQ ID NO 6
<211> LENGTH: 413
<212> TYPE: PRT
<213> ORGANISM: Unknown
<220> FEATURE:
<223> OTHER INFORMATION: isolated from soil sample

<400> SEQUENCE: 6

Met Glu Thr Asp Arg Leu Val Ile Pro Gly Ser Lys Ser Ile Thr Asn
 1               5                  10                  15

Arg Ala Leu Leu Leu Ala Ala Ala Lys Gly Ala Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
```

```
                225                 230                 235                 240
Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Ser Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Met Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 7
<211> LENGTH: 446
<212> TYPE: PRT
<213> ORGANISM: Bacillus clausii

<400> SEQUENCE: 7

Met Val Gln Phe Asp Ser Gln Ala Arg Ser Pro Trp Thr Pro Leu Ala
  1               5                  10                  15

Gly Val Glu Arg Leu Arg Leu Thr Pro Ser Gln Lys Arg Ile Asn Ala
             20                  25                  30

Thr Leu Glu Val Pro Gly Ser Lys Ser Ala Thr Asn Arg Ala Leu Leu
         35                  40                  45

Leu Ala Ala Val Ala Ser Gly Thr Ser Thr Leu Arg Asn Ala Leu Lys
     50                  55                  60

Ser Asp Asp Thr Tyr Trp Cys Ile Glu Ala Leu Lys Lys Thr Gly Val
 65                  70                  75                  80

Glu Ile Ala Val Asp Gly Ser Asn Val Thr Val Tyr Gly Arg Gly Gly
                 85                  90                  95

Val Phe His Ser Gly Ser Leu Tyr Ile Gly Ser Ala Gly Thr Ala Gly
            100                 105                 110

Arg Phe Leu Pro Gly Met Leu Ala Ala Thr Gly Asn Trp His Val
        115                 120                 125

Glu Ala Ser His Ser Met Asn Lys Arg Pro Ile Ala Pro Leu Val Lys
    130                 135                 140

Thr Leu Gln Ala Leu Gly Ala Asn Ile Gln Tyr Gly Ser Arg Arg Gly
145                 150                 155                 160

His Tyr Pro Leu Ser Ile Ser Gly Glu Gly Leu Asn Gly Gly Lys Val
                165                 170                 175

Asn Met Ser Gly Gln Leu Ser Ser Gln Phe Ile Ser Gly Cys Leu Leu
            180                 185                 190
```

Ala Ala Pro Leu Ala Lys Asn Pro Val Ser Ile Thr Val Lys Asp Gly
        195                 200                 205

Ile Val Gln Gln Ala Tyr Val Arg Ile Thr Ile Asp Leu Met Ala Ala
    210                 215                 220

Phe Gly Val Glu Val Lys Ala Ala Pro Asp Trp Ser Leu Leu Glu Val
225                 230                 235                 240

Asn Pro Ser Pro Tyr Val Ala Asn Asp Ile Ala Ile Glu Ala Asp Ala
                245                 250                 255

Ser Thr Ala Cys Tyr Phe Leu Ala Leu Ala Ala Ile Thr Ala Gly Lys
            260                 265                 270

Ile Arg Ile Arg His Phe Ser Thr Lys Thr Ser Gln Pro Asp Ile Leu
        275                 280                 285

Phe Val Ser Ile Leu Lys Arg Met Gly Cys Asn Phe Glu Ile Gly Pro
    290                 295                 300

Ser Phe Val Glu Gly Glu Gly Pro Thr Arg Leu Arg Gly Gly Phe Thr
305                 310                 315                 320

Val Asn Met Asn Glu Leu Ser Asp Gln Ala Leu Thr Leu Ala Ala Ile
                325                 330                 335

Ser Pro Phe Ala Asp Gly Pro Ile Ala Ile Glu Gly Val Gly His Ile
            340                 345                 350

Arg His His Glu Cys Asp Arg Ile Arg Ala Ile Cys Thr Glu Leu Ser
        355                 360                 365

Arg Leu Gly Ile Arg Val Glu Glu Arg His Asp Gly Leu Thr Val Tyr
    370                 375                 380

Pro Gly Gln Pro Lys Pro Thr Val Val Asn Thr Tyr Asp Asp His Arg
385                 390                 395                 400

Met Ala Met Ala Leu Ala Leu Ile Gly Ala Lys Val Asp Gly Ile Glu
                405                 410                 415

Leu Asp Asp Pro Gly Cys Val Ala Lys Thr Cys Pro Ser Tyr Phe Ser
            420                 425                 430

Met Leu Ala Gln Thr Gly Ile Gly Val Lys Ala Val Ser Pro
        435                 440                 445

<210> SEQ ID NO 8
<211> LENGTH: 447
<212> TYPE: PRT
<213> ORGANISM: Rubrobacer xylanophilus

<400> SEQUENCE: 8

Met Ser Gly Val Ser Gly Val Pro Gly Val Asp Phe Gly Ile Glu Glu
1               5                   10                  15

Val Arg Gly Ser Phe Pro Glu Glu Met Glu Val Ala Pro Leu Glu Arg
            20                  25                  30

Pro Pro Asp Ala Thr Val Arg Leu Pro Gly Ser Lys Ser Ile Thr Asn
        35                  40                  45

Arg Ala Leu Leu Val Ala Ala Leu Ala Gly Gly Thr Ser Arg Ile Glu
    50                  55                  60

Asn Pro Leu Leu Ala Asp Asp Pro Phe Trp Leu Met Asn Ala Leu Val
65                  70                  75                  80

Gly Leu Gly Phe Gly Val Arg Val Gly Glu Glu Gly Ala Val Glu Val
                85                  90                  95

Ala Gly Gly Gly Gly Ile Pro Ala Pro Ser Ala Asp Val Phe Val
            100                 105                 110

Gly Asn Ala Gly Thr Val Ala Arg Phe Leu Pro Pro Ala Leu Ala Leu
        115                 120                 125

```
Gly Ser Gly Pro Tyr Arg Val Asp Gly Thr Pro Arg Met Arg Glu Arg
    130                 135                 140

Pro Val Ala Glu Leu Val Glu Ala Leu Arg Ala Leu Gly Ala Arg Val
145                 150                 155                 160

Glu Cys Glu Glu Arg Glu Gly His Leu Pro Leu Val Val Arg Gly Gly
                165                 170                 175

Ala Arg Gly Gly Glu Ile Ser Val Ser Gly Glu Arg Ser Ser Gln
            180                 185                 190

Phe Leu Ser Gly Leu Leu Ile Ser Ala Pro Cys Leu Pro Gly Gly Leu
        195                 200                 205

Thr Val Arg Pro Arg Gly Ala Leu Val Ser Arg Pro Tyr Val Asp Ile
    210                 215                 220

Thr Val Arg Val Met Arg Ser Phe Gly Ala Ser Val Glu Glu Pro
225                 230                 235                 240

Ser Gly Ala Ala Phe Arg Val Ala Pro Gly Ala Tyr Arg Ala Thr Ala
                245                 250                 255

Tyr Arg Val Glu Pro Asp Ala Ser Ala Ala Ser Tyr Phe Leu Ala Ala
            260                 265                 270

Ala Ala Leu Thr Ala Gly Arg Val Val Ile Pro Gly Leu Gly Arg Ser
        275                 280                 285

Ser Leu Gln Gly Asp Val Ala Phe Ala Gly Ile Leu Arg Arg Met Gly
    290                 295                 300

Cys Arg Val Ser Leu Ser Glu Asp Arg Ile Glu Leu Ala Gly Pro Pro
305                 310                 315                 320

Arg Leu Arg Gly Val Glu Ala Asp Met Asn Ala Ile Ser Asp Thr Met
                325                 330                 335

Met Thr Leu Ala Ala Ile Ala Pro Phe Ala Ser Ser Pro Thr Leu Ile
            340                 345                 350

Lys Asn Val Ala His Thr Arg Leu Gln Glu Thr Asp Arg Leu Ala Ala
        355                 360                 365

Val Ala Ala Glu Leu Ser Arg Leu Gly Val Arg Val His Glu Thr Pro
    370                 375                 380

Asp Ser Leu Arg Ile Ile Pro Gly Lys Val Arg Pro Ala Ala Ile Arg
385                 390                 395                 400

Thr Tyr Gly Asp His Arg Met Ala Met Ala Phe Ser Leu Val Gly Leu
                405                 410                 415

Arg Val Arg Gly Val Arg Ile Leu Asp Pro Gly Cys Val Thr Lys Thr
            420                 425                 430

Leu Pro Gly Tyr Phe Arg Leu Leu Glu Gly Leu Arg Arg Gly Gly
        435                 440                 445

<210> SEQ ID NO 9
<211> LENGTH: 444
<212> TYPE: PRT
<213> ORGANISM: Zea mays

<400> SEQUENCE: 9

Ala Gly Ala Glu Glu Ile Val Leu Gln Pro Ile Lys Glu Ile Ser Gly
  1               5                  10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
```

```
                    50                  55                  60
Ser Val Glu Ala Asp Lys Ala Lys Arg Ala Val Val Gly Cys
 65                  70                  75                  80

Gly Gly Lys Phe Pro Val Glu Asp Ala Lys Glu Glu Val Gln Leu Phe
                 85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
            195                 200                 205

Tyr Val Glu Met Thr Leu Arg Leu Met Glu Arg Phe Gly Val Lys Ala
210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
            290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
            370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440

<210> SEQ ID NO 10
<211> LENGTH: 455
<212> TYPE: PRT
<213> ORGANISM: Agrobacterium sp.
```

```
<400> SEQUENCE: 10

Met Ser His Gly Ala Ser Ser Arg Pro Ala Thr Ala Arg Lys Ser Ser
1               5                   10                  15

Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
```

```
                        405                 410                 415
Ser Glu Asn Pro Val Thr Val Asp Asp Ala Thr Met Ile Ala Thr Ser
                420                 425                 430

Phe Pro Glu Phe Met Asp Leu Met Ala Gly Leu Gly Ala Lys Ile Glu
            435                 440                 445

Leu Ser Asp Thr Lys Ala Ala
        450                 455

<210> SEQ ID NO 11
<211> LENGTH: 427
<212> TYPE: PRT
<213> ORGANISM: E. coli

<400> SEQUENCE: 11

Met Glu Ser Leu Thr Leu Gln Pro Ile Ala Arg Val Asp Gly Thr Ile
 1               5                  10                  15

Asn Leu Pro Gly Ser Lys Thr Val Ser Asn Arg Ala Leu Leu Leu Ala
                20                  25                  30

Ala Leu Ala His Gly Lys Thr Val Leu Thr Asn Leu Leu Asp Ser Asp
            35                  40                  45

Asp Val Arg His Met Leu Asn Ala Leu Thr Ala Leu Gly Val Ser Tyr
        50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320
```

```
                Ala Ala Leu Phe Ala Lys Gly Thr Thr Arg Leu Arg Asn Ile Tyr Asn
                                325                 330                 335

Trp Arg Val Lys Glu Thr Asp Arg Leu Phe Ala Met Ala Thr Glu Leu
                                340                 345                 350

Arg Lys Val Gly Ala Glu Val Glu Gly His Asp Tyr Ile Arg Ile
                                355                 360                 365

Thr Pro Pro Glu Lys Leu Asn Phe Ala Glu Ile Ala Thr Tyr Asn Asp
                370                 375                 380

His Arg Met Ala Met Cys Phe Ser Leu Val Ala Leu Ser Asp Thr Pro
                385                 390                 395                 400

Val Thr Ile Leu Asp Pro Lys Cys Thr Ala Lys Thr Phe Pro Asp Tyr
                                405                 410                 415

Phe Glu Gln Leu Ala Arg Ile Ser Gln Ala Ala
                                420                 425

<210> SEQ ID NO 12
<211> LENGTH: 1242
<212> TYPE: DNA
<213> ORGANISM: Artificial Sequence
<220> FEATURE:
<223> OTHER INFORMATION: synthetic grg23
<221> NAME/KEY: CDS
<222> LOCATION: (1)...(1242)

<400> SEQUENCE: 12 atg gaa act gat cgc ctt gtg atc cca gga tcg aaa agc atc acc aac        48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg        96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag       144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa       192
Ala Leu Gly Ala Asn Val Ser Ala Asp Gly Asp Asn Trp Val Val Glu
        50                  55                  60 ggc ctg ggt cag gca ccc cac ctc gac gcc gac atc tgg tgc gag gac       240
Gly Leu Gly Gln Ala Pro His Leu Asp Ala Asp Ile Trp Cys Glu Asp
65                  70                  75                  80 gca ggt act gtg gcc cgg ttc ctc cct cca ttc gta gcc gca ggt cag       288
Ala Gly Thr Val Ala Arg Phe Leu Pro Pro Phe Val Ala Ala Gly Gln
                85                  90                  95 ggg aag ttc acc gtc gac gga tca gag cag ctg cgg cgg cgc ccg ctt       336
Gly Lys Phe Thr Val Asp Gly Ser Glu Gln Leu Arg Arg Arg Pro Leu
                100                 105                 110 cgg ccc ctg gtc gac ggc atc cgc cac ctg ggc gcc cgc gtc tcc tcc       384
Arg Pro Leu Val Asp Gly Ile Arg His Leu Gly Ala Arg Val Ser Ser
            115                 120                 125 gag cag ctg ccc ctt aca att gaa gcg agc ggg ctg gca ggc ggg gag       432
Glu Gln Leu Pro Leu Thr Ile Glu Ala Ser Gly Leu Ala Gly Gly Glu
        130                 135                 140 tac gaa att gaa gcc cat cag agc agc cag ttc gcc tcc ggc ctg atc       480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat       528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac       576
Pro Val Ser Gln Pro Tyr Leu Thr Met Thr Leu Arg Met Met Arg Asp
```

```
                  180                 185                 190
ttc ggc ctt gag acc agc acc gac gga gcc acc gtc agc gtc cct cca    624
Phe Gly Leu Glu Thr Ser Thr Asp Gly Ala Thr Val Ser Val Pro Pro
            195                 200                 205 ggg cgc tac aca gcc cgg cgg tat gaa ata gaa ccg gat gcg tca act    672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa    720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc    768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg    816
Asn Val Leu Gly Arg Leu Gly Ala Glu Val His Trp Ala Pro Asn Ser
            260                 265                 270 gtc acc ata tct gga ccg gaa agg ctg aac ggc gac att gaa gtg gat    864
Val Thr Ile Ser Gly Pro Glu Arg Leu Asn Gly Asp Ile Glu Val Asp
    275                 280                 285 atg ggc gag att tcg gac acc ttc atg aca ctc gcg gcg att gcc cct    912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg    960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc   1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct   1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct   1104
Thr Pro His Gly Gly Arg Val Asn Cys His Arg Asp His Arg Ile Ala
    355                 360                 365 atg gcg ttt tca atc ctg gga ctg aga gtg gac ggg att acc ctc gac   1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt   1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag            1242
Gly Arg Leu Phe Pro Glu Lys Ala Leu Thr Leu Pro Gly *
                405                 410

<210> SEQ ID NO 13
<211> LENGTH: 413
<212> TYPE: PRT
<213> ORGANISM: Artificial Sequence
<220> FEATURE:
<223> OTHER INFORMATION: synthetic grg23

<400> SEQUENCE: 13

Met Glu Thr Asp Arg Leu Val Ile Pro Gly Ser Lys Ser Ile Thr Asn
1               5                   10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
    50                  55                  60
```

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Gly Gln
            85                  90                  95

Gly Lys Phe Thr Val Asp Gly Ser Glu Gln Leu Arg Arg Pro Leu
            100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
            130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
            195                 200                 205

Gly Arg Tyr Thr Ala Arg Arg Tyr Glu Ile Glu Pro Asp Ala Ser Thr
210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
            245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
            275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
            325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 14
<211> LENGTH: 1242
<212> TYPE: DNA
<213> ORGANISM: Artificial Sequence
<220> FEATURE:
<223> OTHER INFORMATION: grg23(ace1)
<221> NAME/KEY: CDS
<222> LOCATION: (1)...(1242)

<400> SEQUENCE: 14

```
atg gaa act gat cgc ctt gtg atc cca gga tcg aaa agc atc acc aac    48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
             20                  25                  30 aga cca ttg gtc agc gcc gat acc tca gca ttc aaa act gca atc cag   144
Arg Pro Leu Val Ser Ala Asp Thr Ser Ala Phe Lys Thr Ala Ile Gln
         35                  40                  45 acc ctc ggt gcc aac gtc tca gcc gac ggt gac aat tgg gtc gtt gaa   192
Thr Leu Gly Ala Asn Val Ser Ala Asp Gly Asp Asn Trp Val Val Glu
     50                  55                  60 ggc ctg ggt cag gca ccc cac ctc gac gcc gac atc tgg tgc gag gac   240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag   288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt   336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc   384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag   432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc   480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat   528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac   576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca   624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act   672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa   720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc   768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg   816
Asn Val Leu Gly Arg Leu Gly Ala Glu Val His Trp Ala Pro Asn Ser
            260                 265                 270 gtc acc ata act gga ccg gaa agg ctg aac ggc gac att gaa gtg gat   864
Val Thr Ile Thr Gly Pro Glu Arg Leu Asn Gly Asp Ile Glu Val Asp
        275                 280                 285 atg ggc gag att tcg gac acc ttc atg aca ctc gcg gcg att gcc cct   912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg   960
Leu Ala Asp Gly Pro Ile Thr Ile Thr Asn Ile Gly His Ala Arg Leu
305                 310                 315                 320
```

```
aag gaa tcc gac cgc atc tca gcg atg gaa acc aac ctg cgc acg ctc      1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct      1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct      1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac      1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt      1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly *
                405                 410
```

<210> SEQ ID NO 15
<211> LENGTH: 413
<212> TYPE: PRT
<213> ORGANISM: Artificial Sequence
<220> FEATURE:
<223> OTHER INFORMATION: grg23(ace1)

<400> SEQUENCE: 15

```
Met Glu Thr Asp Arg Leu Val Ile Pro Gly Ser Lys Ser Ile Thr Asn
 1               5                  10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Thr Leu Gly Ala Asn Val Ser Ala Asp Gly Asp Asn Trp Val Val Glu
    50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240
```

-continued

```
Phe Gln Gly Leu Gly Thr Asp Ser Ile Gln Gly Asp Thr Ser Phe Phe
                245                 250                 255
Asn Val Leu Gly Arg Leu Gly Ala Glu Val His Trp Ala Pro Asn Ser
            260                 265                 270
Val Thr Ile Thr Gly Pro Glu Arg Leu Asn Gly Asp Ile Glu Val Asp
        275                 280                 285
Met Gly Glu Ile Ser Asp Thr Phe Met Thr Leu Ala Ala Ile Ala Pro
    290                 295                 300
Leu Ala Asp Gly Pro Ile Thr Ile Thr Asn Ile Gly His Ala Arg Leu
305                 310                 315                 320
Lys Glu Ser Asp Arg Ile Ser Ala Met Glu Thr Asn Leu Arg Thr Leu
                325                 330                 335
Gly Val Gln Thr Asp Val Gly His Asp Trp Met Arg Ile Tyr Pro Ser
            340                 345                 350
Thr Pro His Gly Gly Arg Val Asn Cys His Arg Asp His Arg Ile Ala
        355                 360                 365
Met Ala Phe Ser Ile Leu Gly Leu Arg Val Asp Gly Ile Thr Leu Asp
    370                 375                 380
Asp Pro Gln Cys Val Gly Lys Thr Phe Pro Gly Phe Phe Asp Tyr Leu
385                 390                 395                 400
Gly Arg Leu Phe Pro Glu Lys Ala Leu Thr Leu Pro Gly
                405                 410
```

<210> SEQ ID NO 16
<211> LENGTH: 1242
<212> TYPE: DNA
<213> ORGANISM: Artificial Sequence
<220> FEATURE:
<223> OTHER INFORMATION: grg23(ace2)
<221> NAME/KEY: CDS
<222> LOCATION: (1)...(1242)

<400> SEQUENCE: 16

```
atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa     192
Ala Leu Gly Ala Asn Val Ser Ala Asp Gly Asp Asn Trp Val Val Glu
        50                  55                  60 ggc ctg ggt cag gca ccc cac ctc gac gcc gac atc tgg tgc gag gac     240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt     336
Gly Lys Phe Thr Val Asp Gly Ser Glu Gln Leu Arg Arg Arg Pro Leu
                100                 105                 110 cgg ccc ctg gtc gac ggc atc cgc cac ctg ggc gcc cgc gtc tcc tcc     384
Arg Pro Leu Val Asp Gly Ile Arg His Leu Gly Ala Arg Val Ser Ser
            115                 120                 125 gag cag ctg ccc ctt aca att gaa gcg agc ggg ctg gca ggc ggg gag     432
```

```
                Glu Gln Leu Pro Leu Thr Ile Glu Ala Ser Gly Leu Ala Gly Gly Glu
                    130                 135                 140 tac gaa att gaa gcc cat cag agc agc cag ttc gcc tcc ggc ctg atc       480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat       528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac       576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca       624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act       672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa       720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc       768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg       816
Asn Val Leu Gly Arg Leu Gly Ala Glu Val His Trp Ala Pro Asn Ser
            260                 265                 270 gtc acc ata cgg gga ccg gaa agg ctg aac ggc gac att gaa gtg gat       864
Val Thr Ile Arg Gly Pro Glu Arg Leu Asn Gly Asp Ile Glu Val Asp
        275                 280                 285 atg ggc gag att tcg gac acc ttc atg aca ctc gcg gcg att gcc cct       912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg       960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc      1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct      1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct      1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac      1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt      1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly  *
                405                 410

<210> SEQ ID NO 17
<211> LENGTH: 413
<212> TYPE: PRT
<213> ORGANISM: Artificial Sequence
<220> FEATURE:
<223> OTHER INFORMATION: grg23(ace2)
```

<400> SEQUENCE: 17

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
                20                  25                  30

Arg Pro Leu Val Ser Ala Asp Thr Ser Ala Phe Lys Thr Ala Ile Gln
             35                  40                  45

Ala Leu Gly Ala Asn Val Ser Ala Asp Gly Asp Asn Trp Val Val Glu
         50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
            100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
            195                 200                 205

Gly Arg Tyr Thr Ala Arg Arg Tyr Glu Ile Glu Pro Asp Ala Ser Thr
210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Arg Gly Pro Glu Arg Leu Asn Gly Asp Ile Glu Val Asp
            275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410
```

<210> SEQ ID NO 18
<211> LENGTH: 1242
<212> TYPE: DNA
<213> ORGANISM: Artificial Sequence
<220> FEATURE:
<223> OTHER INFORMATION: grg51.4
<221> NAME/KEY: CDS
<222> LOCATION: (1)...(1242)

<400> SEQUENCE: 18

| | | | | | | | | | | | | | | | | |
|---|---|---|---|---|---|---|---|---|---|---|---|---|---|---|---|---|
| atg | aaa | act | gat | cga | cta | gtg | atc | cca | gga | tcg | aaa | agc | atc | acc | aac | 48 |
| Met | Glu | Thr | Asp | Arg | Leu | Val | Ile | Pro | Gly | Ser | Lys | Ser | Ile | Thr | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgg | gct | ttg | ctt | ttg | gct | gcc | gca | gcg | aag | ggc | acg | tcg | gtc | ctg | gtg | 96 |
| Arg | Ala | Leu | Leu | Leu | Ala | Ala | Ala | Ala | Lys | Gly | Thr | Ser | Val | Leu | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| aga | cca | ttg | gtc | agc | gcc | gat | acc | tca | gca | ttc | aaa | act | gca | att | cag | 144 |
| Arg | Pro | Leu | Val | Ser | Ala | Asp | Thr | Ser | Ala | Phe | Lys | Thr | Ala | Ile | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | ctc | ggt | gcc | aac | gtc | tca | gcg | gac | ggt | gat | gat | tgg | gtc | gtt | gaa | 192 |
| Ala | Leu | Gly | Ala | Asn | Val | Ser | Ala | Asp | Gly | Asp | Asp | Trp | Val | Val | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | ctg | ggc | cag | gca | ccc | aac | ctc | gac | gcc | gac | atc | tgg | tgc | gag | gat | 240 |
| Gly | Leu | Gly | Gln | Ala | Pro | Asn | Leu | Asp | Ala | Asp | Ile | Trp | Cys | Glu | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gcc | ggt | acc | gtg | gcc | cgg | ttc | ctc | cct | cca | ttc | gtc | gcc | gca | gga | cag | 288 |
| Ala | Gly | Thr | Val | Ala | Arg | Phe | Leu | Pro | Pro | Phe | Val | Ala | Ala | Gly | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| ggg | aag | ttc | acc | gtc | gac | gga | agc | gag | cag | ctg | cgg | cgg | cgc | ccg | ctt | 336 |
| Gly | Lys | Phe | Thr | Val | Asp | Gly | Ser | Glu | Gln | Leu | Arg | Arg | Arg | Pro | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| cgg | ccc | gtg | gtc | gac | ggc | atc | cgc | cac | ctg | ggc | gcc | cgc | gtc | tcc | tcc | 384 |
| Arg | Pro | Val | Val | Asp | Gly | Ile | Arg | His | Leu | Gly | Ala | Arg | Val | Ser | Ser | |
| | | 115 | | | | | 120 | | | | | 125 | | | | |

| | | | | | | | | | | | | | | | | |
|---|---|---|---|---|---|---|---|---|---|---|---|---|---|---|---|---|
| gag | cag | ctg | ccc | cta | acg | att | gaa | gcg | agc | ggg | ctg | gca | ggc | ggg | gag | 432 |
| Glu | Gln | Leu | Pro | Leu | Thr | Ile | Glu | Ala | Ser | Gly | Leu | Ala | Gly | Gly | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| tac | gaa | att | gaa | gcc | cat | cag | agc | agc | cag | ttc | gcc | tcc | ggt | ctg | atc | 480 |
| Tyr | Glu | Ile | Glu | Ala | His | Gln | Ser | Ser | Gln | Phe | Ala | Ser | Gly | Leu | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atg | gcc | gcc | ccg | tac | gcg | cga | caa | ggc | ctg | cgt | gtt | cgg | ata | cca | aat | 528 |
| Met | Ala | Ala | Pro | Tyr | Ala | Arg | Gln | Gly | Leu | Arg | Val | Arg | Ile | Pro | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| ccc | gtg | agc | cag | ccc | tac | ctc | acg | atg | aca | ctg | cgg | atg | atg | agg | gac | 576 |
| Pro | Val | Ser | Gln | Pro | Tyr | Leu | Thr | Met | Thr | Leu | Arg | Met | Met | Arg | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | ggc | att | gag | acc | agc | acc | gac | gga | gcg | acc | gtc | agc | gtt | cct | ccc | 624 |
| Phe | Gly | Ile | Glu | Thr | Ser | Thr | Asp | Gly | Ala | Thr | Val | Ser | Val | Pro | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| ggg | cgc | tac | aca | gcg | cgg | cgg | tat | gag | att | gaa | ccg | gac | gcg | tca | act | 672 |
| Gly | Arg | Tyr | Thr | Ala | Arg | Arg | Tyr | Glu | Ile | Glu | Pro | Asp | Ala | Ser | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| gcg | tcg | tac | ttc | gcc | gcc | gct | tcc | gcc | gtc | tct | ggc | cgg | cgc | ttc | gaa | 720 |
| Ala | Ser | Tyr | Phe | Ala | Ala | Ala | Ser | Ala | Val | Ser | Gly | Arg | Arg | Phe | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttc | cag | ggc | ctt | ggc | aca | gac | agc | atc | caa | ggc | gac | acg | tca | ttc | ttc | 768 |
| Phe | Gln | Gly | Leu | Gly | Thr | Asp | Ser | Ile | Gln | Gly | Asp | Thr | Ser | Phe | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| aat | gta | ctt | ggg | cgg | ctc | ggc | gca | gag | gtc | cac | tgg | gca | tcc | aac | tcg | 816 |
| Asn | Val | Leu | Gly | Arg | Leu | Gly | Ala | Glu | Val | His | Trp | Ala | Ser | Asn | Ser | |

```
                         260                 265                 270
gtc acc ata cgc gga ccg gaa agg ctg acc ggc gac att gaa gtg gat        864
Val Thr Ile Arg Gly Pro Glu Arg Leu Thr Gly Asp Ile Glu Val Asp
            275                 280                 285 atg ggc gag ata tcg gac acc ttc atg aca ctg gcg gcg att gcc cct        912
Met Gly Glu Ile Ser Asp Thr Phe Met Thr Leu Ala Ala Ile Ala Pro
    290                 295                 300 cta gcc gat gga ccc atc acg ata aca aac att ggc cat gca cgg ttg        960
Leu Ala Asp Gly Pro Ile Thr Ile Thr Asn Ile Gly His Ala Arg Leu
305                 310                 315                 320 aag gaa tcc gac cgc atc tcg gcg atg gaa agc aac ctt cga acg ctc       1008
Lys Glu Ser Asp Arg Ile Ser Ala Met Glu Ser Asn Leu Arg Thr Leu
                325                 330                 335 ggt gta caa acc gac gtc gga cac gac tgg atg cga atc tac ccc tct       1056
Gly Val Gln Thr Asp Val Gly His Asp Trp Met Arg Ile Tyr Pro Ser
            340                 345                 350 acc ccg cac ggc ggc aga gtc aat tgc cac cgg gac cac agg atc gcc       1104
Thr Pro His Gly Gly Arg Val Asn Cys His Arg Asp His Arg Ile Ala
        355                 360                 365 atg gcg ttt tca atc ctg gga ctg cga gtg gac ggg att acc ctc gac       1152
Met Ala Phe Ser Ile Leu Gly Leu Arg Val Asp Gly Ile Thr Leu Asp
    370                 375                 380 gac cct caa tgt gtc ggg aag acc ttt cct ggc ttc ttc gac tac ctt       1200
Asp Pro Gln Cys Val Gly Lys Thr Phe Pro Gly Phe Phe Asp Tyr Leu
385                 390                 395                 400 gga cgc ctt ttc ccg gaa aag gcg ctt acg ctc ccc ggc tag               1242
Gly Arg Leu Phe Pro Glu Lys Ala Leu Thr Leu Pro Gly  *
                405                 410

<210> SEQ ID NO 19
<211> LENGTH: 413
<212> TYPE: PRT
<213> ORGANISM: Artificial Sequence
<220> FEATURE:
<223> OTHER INFORMATION: grg51.4

<400> SEQUENCE: 19

Met Glu Thr Asp Arg Leu Val Ile Pro Gly Ser Lys Ser Ile Thr Asn
1               5                   10                  15

Arg Ala Leu Leu Leu Ala Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
```

```
                    165                 170                 175
Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
            195                 200                 205

Gly Arg Tyr Thr Ala Arg Arg Tyr Glu Ile Glu Pro Asp Ala Ser Thr
            210                 215                 220

Ala Ser Tyr Phe Ala Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
            275                 280                 285

Met Gly Glu Ile Ser Asp Thr Phe Met Thr Leu Ala Ala Ile Ala Pro
            290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
            370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 20
<211> LENGTH: 1242
<212> TYPE: DNA
<213> ORGANISM: Artificial Sequence
<220> FEATURE:
<223> OTHER INFORMATION: grg23(ace3)
<221> NAME/KEY: CDS
<222> LOCATION: (1)...(1242)

<400> SEQUENCE: 20 atg gaa act gat cgc ctt gtg atc cca gga tcg aaa agc atc acc aac      48
Met Glu Thr Asp Arg Leu Val Ile Pro Gly Ser Lys Ser Ile Thr Asn
1               5                   10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
            35                  40                  45 gcc ctc ggt gcc aac gtc tca gcc gac ggt gac gat tgg gtc gtt gaa     192
Ala Leu Gly Ala Asn Val Ser Ala Asp Gly Asp Asp Trp Val Val Glu
        50                  55                  60 ggc ctg ggt cag gca ccc aac ctc gac gcc gac atc tgg tgc gag gac     240
Gly Leu Gly Gln Ala Pro Asn Leu Asp Ala Asp Ile Trp Cys Glu Asp
65                  70                  75                  80
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gca | ggt | act | gtg | gcc | cgg | ttc | ctc | cct | cca | ttc | gta | gcc | gca | ggt | cag | 288 |
| Ala | Gly | Thr | Val | Ala | Arg | Phe | Leu | Pro | Pro | Phe | Val | Ala | Ala | Gly | Gln |     |
|     |     |     |     | 85  |     |     |     |     | 90  |     |     |     |     | 95  |     |     |
| ggg | aag | ttc | acc | gtc | gac | gga | tca | gag | cag | ctg | cgg | cgc | cgc | ccg | ctt | 336 |
| Gly | Lys | Phe | Thr | Val | Asp | Gly | Ser | Glu | Gln | Leu | Arg | Arg | Arg | Pro | Leu |     |
|     |     |     | 100 |     |     |     |     | 105 |     |     |     |     | 110 |     |     |     |
| cgg | ccc | gtg | gtc | gac | ggc | atc | cgc | cac | ctg | ggc | gcc | cgc | gtc | tcc | tcc | 384 |
| Arg | Pro | Val | Val | Asp | Gly | Ile | Arg | His | Leu | Gly | Ala | Arg | Val | Ser | Ser |     |
|     | 115 |     |     |     |     | 120 |     |     |     |     | 125 |     |     |     |     |     |
| gag | cag | ctg | ccc | ctt | aca | att | gaa | gcg | agc | ggg | ctg | gca | ggc | ggg | gag | 432 |
| Glu | Gln | Leu | Pro | Leu | Thr | Ile | Glu | Ala | Ser | Gly | Leu | Ala | Gly | Gly | Glu |     |
| 130 |     |     |     |     | 135 |     |     |     |     | 140 |     |     |     |     |     |     |
| tac | gaa | att | gaa | gcc | cat | cag | agc | agc | cag | ttc | gcc | tcc | ggc | ctg | atc | 480 |
| Tyr | Glu | Ile | Glu | Ala | His | Gln | Ser | Ser | Gln | Phe | Ala | Ser | Gly | Leu | Ile |     |
| 145 |     |     |     |     | 150 |     |     |     |     | 155 |     |     |     |     | 160 |     |
| atg | gcc | gcc | ccg | tac | gcg | aga | caa | ggc | ctg | cgt | gtg | cgg | ata | cca | aat | 528 |
| Met | Ala | Ala | Pro | Tyr | Ala | Arg | Gln | Gly | Leu | Arg | Val | Arg | Ile | Pro | Asn |     |
|     |     |     |     | 165 |     |     |     |     | 170 |     |     |     |     | 175 |     |     |
| ccc | gtg | tca | cag | ccc | tac | ctc | acg | atg | aca | ctg | cgg | atg | atg | agg | gac | 576 |
| Pro | Val | Ser | Gln | Pro | Tyr | Leu | Thr | Met | Thr | Leu | Arg | Met | Met | Arg | Asp |     |
|     |     || 180 |     |     |     |     | 185 |     |     |     |     | 190 |     |     |     |     |
| ttc | ggc | att | gag | acc | agc | acc | gac | gga | gcc | acc | gtc | agc | gtc | cct | cca | 624 |
| Phe | Gly | Ile | Glu | Thr | Ser | Thr | Asp | Gly | Ala | Thr | Val | Ser | Val | Pro | Pro |     |
|     |     |     | 195 |     |     |     |     | 200 |     |     |     |     | 205 |     |     |     |
| ggg | cgc | tac | aca | gcc | cgg | cgg | tat | gaa | ata | gaa | ccg | gat | gcg | tca | act | 672 |
| Gly | Arg | Tyr | Thr | Ala | Arg | Arg | Tyr | Glu | Ile | Glu | Pro | Asp | Ala | Ser | Thr |     |
|     |     | 210 |     |     |     |     | 215 |     |     |     |     | 220 |     |     |     |     |
| gcg | tcg | tac | ttc | gcc | gcc | gct | tcc | gcc | gtc | tct | ggc | agg | cgc | ttc | gaa | 720 |
| Ala | Ser | Tyr | Phe | Ala | Ala | Ala | Ser | Ala | Val | Ser | Gly | Arg | Arg | Phe | Glu |     |
| 225 |     |     |     |     | 230 |     |     |     |     | 235 |     |     |     |     | 240 |     |
| ttt | caa | ggc | ctt | ggc | aca | gac | agc | atc | caa | ggc | gac | acg | tca | ttc | ttc | 768 |
| Phe | Gln | Gly | Leu | Gly | Thr | Asp | Ser | Ile | Gln | Gly | Asp | Thr | Ser | Phe | Phe |     |
|     |     |     |     | 245 |     |     |     |     | 250 |     |     |     |     | 255 |     |     |
| aat | gta | ctt | ggg | cgg | ctc | ggt | gcg | gag | gtc | cac | tgg | gca | tcc | aac | tcg | 816 |
| Asn | Val | Leu | Gly | Arg | Leu | Gly | Ala | Glu | Val | His | Trp | Ala | Ser | Asn | Ser |     |
|     |     |     | 260 |     |     |     |     | 265 |     |     |     |     | 270 |     |     |     |
| gtc | acc | ata | cgt | gga | ccg | gaa | agg | ctg | acc | ggc | gac | att | gaa | gtg | gat | 864 |
| Val | Thr | Ile | Arg | Gly | Pro | Glu | Arg | Leu | Thr | Gly | Asp | Ile | Glu | Val | Asp |     |
|     |     | 275 |     |     |     |     | 280 |     |     |     |     | 285 |     |     |     |     |
| atg | ggc | gag | att | tcg | gac | acc | ttc | atg | aca | ctc | gcg | gcg | att | gcc | cct | 912 |
| Met | Gly | Glu | Ile | Ser | Asp | Thr | Phe | Met | Thr | Leu | Ala | Ala | Ile | Ala | Pro |     |
|     | 290 |     |     |     |     | 295 |     |     |     |     | 300 |     |     |     |     |     |
| ttg | gcc | gat | gga | ccc | atc | acg | ata | acc | aac | att | ggt | cat | gca | cgg | ttg | 960 |
| Leu | Ala | Asp | Gly | Pro | Ile | Thr | Ile | Thr | Asn | Ile | Gly | His | Ala | Arg | Leu |     |
| 305 |     |     |     |     | 310 |     |     |     |     | 315 |     |     |     |     | 320 |     |
| aag | gaa | tcc | gac | cgc | atc | tca | gcg | atg | gaa | agc | aac | ctg | cgc | acg | ctc | 1008 |
| Lys | Glu | Ser | Asp | Arg | Ile | Ser | Ala | Met | Glu | Ser | Asn | Leu | Arg | Thr | Leu |     |
|     |     |     |     | 325 |     |     |     |     | 330 |     |     |     |     | 335 |     |     |
| ggt | gta | caa | acc | gac | gtc | gga | cac | gac | tgg | atg | aga | atc | tac | ccc | tct | 1056 |
| Gly | Val | Gln | Thr | Asp | Val | Gly | His | Asp | Trp | Met | Arg | Ile | Tyr | Pro | Ser |     |
|     |     |     | 340 |     |     |     |     | 345 |     |     |     |     | 350 |     |     |     |
| acc | ccg | cac | ggc | ggt | aga | gtg | aat | tgc | cac | cgg | gac | cac | agg | atc | gct | 1104 |
| Thr | Pro | His | Gly | Gly | Arg | Val | Asn | Cys | His | Arg | Asp | His | Arg | Ile | Ala |     |
|     |     | 355 |     |     |     |     | 360 |     |     |     |     | 365 |     |     |     |     |
| atg | gcg | ttt | tca | atc | ctg | gga | ctg | aga | gtg | gac | ggg | att | acc | ctc | gac | 1152 |
| Met | Ala | Phe | Ser | Ile | Leu | Gly | Leu | Arg | Val | Asp | Gly | Ile | Thr | Leu | Asp |     |
|     | 370 |     |     |     |     | 375 |     |     |     |     | 380 |     |     |     |     |     |
| gac | cct | caa | tgc | gtc | ggg | aag | acc | ttt | cct | ggc | ttc | ttc | gac | tac | ctt | 1200 |
| Asp | Pro | Gln | Cys | Val | Gly | Lys | Thr | Phe | Pro | Gly | Phe | Phe | Asp | Tyr | Leu |     |
| 385 |     |     |     |     | 390 |     |     |     |     | 395 |     |     |     |     | 400 |     |

```
gga cgc ctt ttc ccc gaa aag gcg ctt acg ctc ccc ggc tag        1242
Gly Arg Leu Phe Pro Glu Lys Ala Leu Thr Leu Pro Gly  *
            405                 410
```

<210> SEQ ID NO 21
<211> LENGTH: 413
<212> TYPE: PRT
<213> ORGANISM: Artificial Sequence
<220> FEATURE:
<223> OTHER INFORMATION: grg23(ace3)

<400> SEQUENCE: 21

```
Met Glu Thr Asp Arg Leu Val Ile Pro Gly Ser Lys Ser Ile Thr Asn
  1               5                  10                  15

Arg Ala Leu Leu Leu Ala Ala Ala Lys Gly Thr Ser Val Leu Val
             20                  25                  30

Arg Pro Leu Val Ser Ala Asp Thr Ser Ala Phe Lys Thr Ala Ile Gln
         35                  40                  45

Ala Leu Gly Ala Asn Val Ser Ala Asp Gly Asp Asp Trp Val Val Glu
     50                  55                  60

Gly Leu Gly Gln Ala Pro Asn Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270

Val Thr Ile Arg Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
```

```
                340               345               350
Thr Pro His Gly Gly Arg Val Asn Cys His Arg Asp His Arg Ile Ala
            355               360               365

Met Ala Phe Ser Ile Leu Gly Leu Arg Val Asp Gly Ile Thr Leu Asp
        370               375               380

Asp Pro Gln Cys Val Gly Lys Thr Phe Pro Gly Phe Phe Asp Tyr Leu
385               390               395               400

Gly Arg Leu Phe Pro Glu Lys Ala Leu Thr Leu Pro Gly
                405               410

<210> SEQ ID NO 22
<211> LENGTH: 1242
<212> TYPE: DNA
<213> ORGANISM: Artificial Sequence
<220> FEATURE:
<223> OTHER INFORMATION: grg23(L5P2.J2)
<221> NAME/KEY: CDS
<222> LOCATION: (1)...(1242)

<400> SEQUENCE: 22 atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtg ctg gtg      96
Arg Ala Leu Leu Leu Ala Ala Ala Ala Lys Gly Thr Ser Val Leu Val
             20                  25                  30 aga cca ttg gtc agc gcc gat acc tca gca ttc aaa act gca atc cag     144
Arg Pro Leu Val Ser Ala Asp Thr Ser Ala Phe Lys Thr Ala Ile Gln
         35                  40                  45 acc ctc ggt gcc aac gtc tca gcc gac ggt gac aat tgg gtc gtt gaa     192
Thr Leu Gly Ala Asn Val Ser Ala Asp Gly Asp Asn Trp Val Val Glu
     50                  55                  60 ggc ctg ggt cag gca ccc cac ctc gac gcc gac atc tgg tgc gag gac     240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag     288
Ala Gly Thr Val Ala Arg Phe Leu Pro Pro Phe Val Ala Ala Gly Gln
                 85                  90                  95 ggg aag ttc acc ttc gac gga tca gag cag ctg cgg cgg cgc ccg ctt     336
Gly Lys Phe Thr Phe Asp Gly Ser Glu Gln Leu Arg Arg Arg Pro Leu
            100                 105                 110 cgg ccc ctg gtc gac ggc atc cgc cac ctg ggc gcc cgc gtc tcc tcc     384
Arg Pro Leu Val Asp Gly Ile Arg His Leu Gly Ala Arg Val Ser Ser
        115                 120                 125 gag cag ctg ccc ctt aca att gaa gcg agt ggg ctg gca ggc ggg gag     432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc     480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat     528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac     576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca     624
Phe Gly Leu Glu Thr Ser Thr Asp Gly Ala Thr Val Ser Val Pro Pro
        195                 200                 205 ggg cgc tac aca tcc cgg cgg tat gaa ata gaa ccg gat gcg tca act     672
```

```
                                                                                  -continued Gly Arg Tyr Thr Ser Arg Arg Tyr Glu Ile Glu Pro Asp Ala Ser Thr
            210                 215                 220 gcg tcg tac ttc gcc gcc gct tcc gcc gtc tct ggc agg agc ttc gaa        720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc        768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg        816
Asn Val Leu Gly Arg Leu Gly Ala Glu Val His Trp Ala Pro Asn Ser
            260                 265                 270 gtc acc ata act gga ccg gaa agg ctg aac ggc aac att gaa gtg gat        864
Val Thr Ile Thr Gly Pro Glu Arg Leu Asn Gly Asn Ile Glu Val Asp
        275                 280                 285 atg ggc gag att tcg gac acc ttc atg aca ctc gcg gcg att gcc cct        912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg        960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc       1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct       1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct       1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac       1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt       1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly *
                405                 410

<210> SEQ ID NO 23
<211> LENGTH: 413
<212> TYPE: PRT
<213> ORGANISM: Artificial Sequence
<220> FEATURE:
<223> OTHER INFORMATION: grg23(L5P2.J2)

<400> SEQUENCE: 23

Met Glu Thr Asp Arg Leu Val Ile Pro Gly Ser Lys Ser Ile Thr Asn
1               5                   10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Thr Leu Gly Ala Asn Val Ser Ala Asp Gly Asp Asn Trp Val Val Glu
    50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95
```

```
Gly Lys Phe Thr Phe Asp Gly Ser Glu Gln Leu Arg Arg Arg Pro Leu
                100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
        130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ser Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Thr Gly Pro Glu Arg Leu Asn Gly Asn Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 24
<211> LENGTH: 1242
<212> TYPE: DNA
<213> ORGANISM: Artificial Sequence
<220> FEATURE:
<223> OTHER INFORMATION: grg23(ace4)
<221> NAME/KEY: CDS
<222> LOCATION: (1)...(1242)

<400> SEQUENCE: 24 atg gaa act gat cgc ctt gtg atc cca gga tcg aaa agc atc acc aac      48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg      96
Arg Ala Leu Leu Leu Ala Ala Ala Ala Lys Gly Thr Ser Val Leu Val
            20                  25                  30
```

-continued

```
aga cca ttg gtc agc gcc gat acc tca gca ttc aaa act gca atc cag    144
Arg Pro Leu Val Ser Ala Asp Thr Ser Ala Phe Lys Thr Ala Ile Gln
         35                  40                  45 gcc ctc ggt gcc aac gtc tca gcc gac ggt gac gat tgg gtc gtt gaa    192
Ala Leu Gly Ala Asn Val Ser Ala Asp Gly Asp Asp Trp Val Val Glu
 50                  55                  60 ggc ctg ggt cag gca ccc aac ctc gac gcc gac atc tgg tgc gag gac    240
Gly Leu Gly Gln Ala Pro Asn Leu Asp Ala Asp Ile Trp Cys Glu Asp
 65                  70                  75                  80 gca ggt act gtg gcc cgg ttc ctc cct cca ttc gta gcc gca ggt cag    288
Ala Gly Thr Val Ala Arg Phe Leu Pro Pro Phe Val Ala Ala Gly Gln
                 85                  90                  95 ggg aag ttc acc ttc gac gga tca gag cag ctg cgg cgg cgc ccg ctt    336
Gly Lys Phe Thr Phe Asp Gly Ser Glu Gln Leu Arg Arg Arg Pro Leu
            100                 105                 110 cgg ccc gtg gtc gac ggc atc cgc cac ctg ggc gcc cgc gtc tcc tcc    384
Arg Pro Val Val Asp Gly Ile Arg His Leu Gly Ala Arg Val Ser Ser
        115                 120                 125 gag cag ctg ccc ctt aca att gaa gcg agc ggg ctg gca ggc ggg gag    432
Glu Gln Leu Pro Leu Thr Ile Glu Ala Ser Gly Leu Ala Gly Gly Glu
130                 135                 140 tac gaa att gaa gcc cat cag agc agc cag ttc gcc tcc ggc ctg atc    480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat    528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac    576
Pro Val Ser Gln Pro Tyr Leu Thr Met Thr Leu Arg Met Met Arg Asp
            180                 185                 190 ttc ggc att gag acc agc acc gac gga gcc acc gtc agc gtc cct cca    624
Phe Gly Ile Glu Thr Ser Thr Asp Gly Ala Thr Val Ser Val Pro Pro
        195                 200                 205 ggg cgc tac aca gcc cgg cgg tat gaa ata gaa ccg gat gcg tca act    672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg cgc ttc gaa    720
Ala Ser Tyr Phe Ala Ala Ala Ser Ala Val Ser Gly Arg Arg Phe Glu
225                 230                 235                 240 ttt caa ggc ctt ggc aca gac agc atc caa ggc gac acg tca ttc ttc    768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca tcc aac tcg    816
Asn Val Leu Gly Arg Leu Gly Ala Glu Val His Trp Ala Ser Asn Ser
            260                 265                 270 gtc acc ata cgg gga ccg gaa agg ctg acc ggc gac att gaa gtg gat    864
Val Thr Ile Arg Gly Pro Glu Arg Leu Thr Gly Asp Ile Glu Val Asp
        275                 280                 285 atg ggc gag att tcg gac acc ttc atg aca ctc gcg gcg att gcc cct    912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg    960
Leu Ala Asp Gly Pro Ile Thr Ile Thr Asn Ile Gly His Ala Arg Leu
305                 310                 315                 320 aag gaa tcc gac cgc atc tca gcg atg gaa agc aac ctg cgc acg ctc   1008
Lys Glu Ser Asp Arg Ile Ser Ala Met Glu Ser Asn Leu Arg Thr Leu
                325                 330                 335 ggt gta caa acc gac gtc gga cac gac tgg atg aga atc tac ccc tct   1056
Gly Val Gln Thr Asp Val Gly His Asp Trp Met Arg Ile Tyr Pro Ser
```

```
                      340                 345                 350
acc ccg cac ggc ggt aga gtg aat tgc cac cgg gac cac agg atc gct      1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac      1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt      1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly  *
            405                 410
```

<210> SEQ ID NO 25
<211> LENGTH: 413
<212> TYPE: PRT
<213> ORGANISM: Artificial Sequence
<220> FEATURE:
<223> OTHER INFORMATION: grg23(ace4)

<400> SEQUENCE: 25

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Trp Val Val Glu
    50                  55                  60

Gly Leu Gly Gln Ala Pro Asn Leu Asp Ala Asp Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Phe Asp Gly Ser Glu Gln Leu Arg Arg Pro Leu
            100                 105                 110

Arg Pro Val Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Ile Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ser Ala Val Ser Gly Arg Arg Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Ser Asn Ser
            260                 265                 270
```

```
Val Thr Ile Arg Gly Pro Glu Arg Leu Thr Gly Asp Ile Glu Val Asp
        275                 280                 285

Met Gly Glu Ile Ser Asp Thr Phe Met Thr Leu Ala Ala Ile Ala Pro
        290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Ser Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
        370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410
```

```
<210> SEQ ID NO 26
<211> LENGTH: 1244
<212> TYPE: DNA
<213> ORGANISM: Artificial Sequence
<220> FEATURE:
<223> OTHER INFORMATION: grg23(L3P1.B20)
<221> NAME/KEY: CDS
<222> LOCATION: (1)...(1242)

<400> SEQUENCE: 26
```

```
atg gaa act gat cgc ctt gtg atc cca gga tcg aaa agc atc acc aac    48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg    96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag   144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa   192
Ala Leu Gly Ala Asn Val Ser Ala Asp Gly Asp Asn Trp Val Val Glu
        50                  55                  60 ggc ctg ggt cag gca ccc cac ctc gac gcc gac atc tgg tgc gag gac   240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag   288
Ala Gly Thr Val Ala Arg Phe Leu Pro Pro Phe Val Ala Ala Gly Gln
                 85                  90                  95 ggg aag ttc acc gtc gac gga tca gag cag ttg cgg cgg cgc ccg ctt   336
Gly Lys Phe Thr Val Asp Gly Ser Glu Gln Leu Arg Arg Arg Pro Leu
                100                 105                 110 cgg ccc ctg gtt gac ggc atc cgc cac ctg ggc gcc cgc gtc tcc tcc   384
Arg Pro Leu Val Asp Gly Ile Arg His Leu Gly Ala Arg Val Ser Ser
            115                 120                 125 gag cag ctg ccc ctt aca att gaa gcg agc ggg ctg gca ggc ggg gag   432
Glu Gln Leu Pro Leu Thr Ile Glu Ala Ser Gly Leu Ala Gly Gly Glu
        130                 135                 140 tac gaa att gaa gcc cat cag agc agc cag ttc gcc tcc ggc ctg atc   480
Tyr Glu Ile Glu Ala His Gln Ser Ser Gln Phe Ala Ser Gly Leu Ile
145                 150                 155                 160
```

```
atg gcc gcc ccg tac gcg aga caa ggc ctg cgt gtg cgg ata cca aat       528
Met Ala Ala Pro Tyr Ala Arg Gln Gly Leu Arg Val Arg Ile Pro Asn
            165                 170                 175 ccc gtg tca cag ccc tac ctc acg atg aca ctg cgg atg atg agg gac       576
Pro Val Ser Gln Pro Tyr Leu Thr Met Thr Leu Arg Met Met Arg Asp
        180                 185                 190 ttc ggc ctt gag acc agc acc gac gga gcc acc gtc agc atc cct cca       624
Phe Gly Leu Glu Thr Ser Thr Asp Gly Ala Thr Val Ser Ile Pro Pro
    195                 200                 205 ggg cgc tac aca gcc cgg cgg tat gaa ata gaa ccg gat gcg tca act       672
Gly Arg Tyr Thr Ala Arg Arg Tyr Glu Ile Glu Pro Asp Ala Ser Thr
210                 215                 220 gcg tcg tac ttc gcc gcc gct tcc gcc gtc tct ggc agg agc ttc gaa       720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc       768
Phe Gln Gly Leu Gly Thr Asp Ser Ile Gln Gly Asp Thr Ser Phe Phe
            245                 250                 255 aat gta ctt ggg cgg ctc ggt gcg gag gtc cac tgg gca ccc aac tcg       816
Asn Val Leu Gly Arg Leu Gly Ala Glu Val His Trp Ala Pro Asn Ser
        260                 265                 270 gtc acc ata tct gga ccg gaa agg ctg aac ggc gac att gaa gtg gat       864
Val Thr Ile Ser Gly Pro Glu Arg Leu Asn Gly Asp Ile Glu Val Asp
    275                 280                 285 atg ggc gag att tcg gac acc ttc atg aca ctc gcg gcg att gcc cct       912
Met Gly Glu Ile Ser Asp Thr Phe Met Thr Leu Ala Ala Ile Ala Pro
290                 295                 300 ttg gcc gat gga ccc atc acg ata acc aac att ggt cat gca cgg ttg       960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc      1008
Lys Glu Ser Asp Arg Ile Ser Ala Met Glu Thr Asn Leu Arg Thr Leu
            325                 330                 335 ggt gta caa acc gac gtc gga cac gac tgg atg aga atc tac ccc tct      1056
Gly Val Gln Thr Asp Val Gly His Asp Trp Met Arg Ile Tyr Pro Ser
        340                 345                 350 acc ccg cac ggc ggt aga gtg aat tgc cac cgg gac cac agg atc gct      1104
Thr Pro His Gly Gly Arg Val Asn Cys His Arg Asp His Arg Ile Ala
    355                 360                 365 atg gcg ttt tca atc ctg gga ctg aga gtg gac ggg att acc ctc gac      1152
Met Ala Phe Ser Ile Leu Gly Leu Arg Val Asp Gly Ile Thr Leu Asp
370                 375                 380 gac cct caa tgc gtc ggg aag acc ttt cct ggc ttc ttc gac tac ctt      1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag             1242
Gly Arg Leu Phe Pro Glu Lys Ala Leu Thr Leu Pro Gly *
            405                 410 gg                                                                  1244

<210> SEQ ID NO 27
<211> LENGTH: 413
<212> TYPE: PRT
<213> ORGANISM: Artificial Sequence
<220> FEATURE:
<223> OTHER INFORMATION: grg23(L3P1.B20)

<400> SEQUENCE: 27

Met Glu Thr Asp Arg Leu Val Ile Pro Gly Ser Lys Ser Ile Thr Asn
1               5                   10                  15
```

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
50                  55                  60

Gly Leu Gly Gln Ala Pro His Leu Asp Ala Asp Ile Trp Cys Glu Asp
65                  70                  75                  80

Ala Gly Thr Val Ala Arg Phe Leu Pro Pro Phe Val Ala Gly Gln
            85                  90                  95

Gly Lys Phe Thr Val Asp Gly Ser Glu Gln Leu Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
            165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Ile Pro Pro
            195                 200                 205

Gly Arg Tyr Thr Ala Arg Arg Tyr Glu Ile Glu Pro Asp Ala Ser Thr
210                 215                 220

Ala Ser Tyr Phe Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
            245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
            275                 280                 285

Met Gly Glu Ile Ser Asp Thr Phe Met Thr Leu Ala Ala Ile Ala Pro
290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
            325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
            355                 360                 365

Met Ala Phe Ser Ile Leu Gly Leu Arg Val Asp Gly Ile Thr Leu Asp
            370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
            405                 410

<210> SEQ ID NO 28
<211> LENGTH: 1244
<212> TYPE: DNA

<213> ORGANISM: Artificial Sequence
<220> FEATURE:
<223> OTHER INFORMATION: grg23(L3P1.B3)
<221> NAME/KEY: CDS
<222> LOCATION: (1)...(1242)

<400> SEQUENCE: 28

```
atg gaa act gat cgc ctt gtg atc cca gga tcg aaa agc atc acc aac        48
Met Glu Thr Asp Arg Leu Val Ile Pro Gly Ser Lys Ser Ile Thr Asn
 1               5                  10                  15 cgg gct ttg ctt ttg gct gcc gca gcg aag ggc acg tcg gtc ctg gtg        96
Arg Ala Leu Leu Leu Ala Ala Ala Ala Lys Gly Thr Ser Val Leu Val
                20                  25                  30 aga cca ttg gtc agc gcc gat acc tca gca ttc aaa act gca atc cag       144
Arg Pro Leu Val Ser Ala Asp Thr Ser Ala Phe Lys Thr Ala Ile Gln
            35                  40                  45 gcc ctc ggt gcc aac gtc tca gcc gac ggt gac aat tgg gtc gtt gaa       192
Ala Leu Gly Ala Asn Val Ser Ala Asp Gly Asp Asn Trp Val Val Glu
        50                  55                  60 ggc ctg ggt cag gca ccc cac ctc gac gcc cac atc tgg tgc gag gac       240
Gly Leu Gly Gln Ala Pro His Leu Asp Ala His Ile Trp Cys Glu Asp
 65                  70                  75                  80 gca ggt act gtg gcc cgg ttc ctc cct cca ttc gta gcc gca ggt cag       288
Ala Gly Thr Val Ala Arg Phe Leu Pro Pro Phe Val Ala Ala Gly Gln
                 85                  90                  95 ggg aag ttc acc gtc gac gga tca gag cag ctg cgg cgg cgc ccg ctt       336
Gly Lys Phe Thr Val Asp Gly Ser Glu Gln Leu Arg Arg Arg Pro Leu
                100                 105                 110 cgg ccc ctg gtc gac ggc atc cgc cac ctg ggc gcc cgc gtc tcc tcc       384
Arg Pro Leu Val Asp Gly Ile Arg His Leu Gly Ala Arg Val Ser Ser
            115                 120                 125 gag cag ctg ccc ctt aca att gaa gcg agc ggg ctg gca ggc ggg gag       432
Glu Gln Leu Pro Leu Thr Ile Glu Ala Ser Gly Leu Ala Gly Gly Glu
        130                 135                 140 tac gaa att gaa gcc cat cag agc agc cag ttc gcc tcc ggc ctg atc       480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat       528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac       576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca       624
Phe Gly Leu Glu Thr Ser Thr Asp Gly Ala Thr Val Ser Val Pro Pro
        195                 200                 205 ggg cgc tac aca gcc cgg cgg tat aaa ata gaa ccg gat gcg tca act       672
Gly Arg Tyr Thr Ala Arg Arg Tyr Lys Ile Glu Pro Asp Ala Ser Thr
    210                 215                 220 gcg tcg tac ttc gcc gcc gct tcc gcc gtc tct ggc agg agc ttc gaa       720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc       768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg       816
Asn Val Leu Gly Arg Leu Gly Ala Glu Val His Trp Ala Pro Asn Ser
            260                 265                 270 gtc acc ata tct gga ccg gaa agg ctg aac ggc gac att gaa gtg gat       864
Val Thr Ile Ser Gly Pro Glu Arg Leu Asn Gly Asp Ile Glu Val Asp
        275                 280                 285
```

```
atg ggc gag att tcg gac acc ttc atg aca ctc gcg gcg att gcc cct        912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg        960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc       1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct       1056
Gly Val Gln Thr Asp Val Gly His Asp Trp Met Arg Ile Tyr Pro Ser
            340                 345                 350 acc ccg cac ggc ggt aga gtg aat tgc cac cga gac cac agg atc gct       1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac       1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt       1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag              1242
Gly Arg Leu Phe Pro Glu Lys Ala Leu Thr Leu Pro Gly *
                405                 410 gg                                                                    1244
```

<210> SEQ ID NO 29
<211> LENGTH: 413
<212> TYPE: PRT
<213> ORGANISM: Artificial Sequence
<220> FEATURE:
<223> OTHER INFORMATION: grg23(L3P1.B3)

<400> SEQUENCE: 29

```
Met Glu Thr Asp Arg Leu Val Ile Pro Gly Ser Lys Ser Ile Thr Asn
 1               5                  10                  15

Arg Ala Leu Leu Leu Ala Ala Ala Lys Gly Thr Ser Val Leu Val
            20                  25                  30

Arg Pro Leu Val Ser Ala Asp Thr Ser Ala Phe Lys Thr Ala Ile Gln
        35                  40                  45

Ala Leu Gly Ala Asn Val Ser Ala Asp Gly Asp Asn Trp Val Val Glu
    50                  55                  60

Gly Leu Gly Gln Ala Pro His Leu Asp Ala His Ile Trp Cys Glu Asp
65                  70                  75                  80

Ala Gly Thr Val Ala Arg Phe Leu Pro Pro Phe Val Ala Ala Gly Gln
                85                  90                  95

Gly Lys Phe Thr Val Asp Gly Ser Glu Gln Leu Arg Arg Pro Leu
                100                 105                 110

Arg Pro Leu Val Asp Gly Ile Arg His Leu Gly Ala Arg Val Ser Ser
            115                 120                 125

Glu Gln Leu Pro Leu Thr Ile Glu Ala Ser Gly Leu Ala Gly Gly Glu
        130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
```

```
                    180                 185                 190
    Phe Gly Leu Glu Thr Ser Thr Asp Gly Ala Thr Val Ser Val Pro Pro
                195                 200                 205

Gly Arg Tyr Thr Ala Arg Arg Tyr Lys Ile Glu Pro Asp Ala Ser Thr
            210                 215                 220

Ala Ser Tyr Phe Ala Ala Ser Ala Val Ser Gly Arg Ser Phe Glu
    225                 230                 235                 240

Phe Gln Gly Leu Gly Thr Asp Ser Ile Gln Gly Asp Thr Ser Phe Phe
                    245                 250                 255

Asn Val Leu Gly Arg Leu Gly Ala Glu Val His Trp Ala Pro Asn Ser
                260                 265                 270

Val Thr Ile Ser Gly Pro Glu Arg Leu Asn Gly Asp Ile Glu Val Asp
                275                 280                 285

Met Gly Glu Ile Ser Asp Thr Phe Met Thr Leu Ala Ala Ile Ala Pro
                290                 295                 300

Leu Ala Asp Gly Pro Ile Thr Ile Thr Asn Ile Gly His Ala Arg Leu
    305                 310                 315                 320

Lys Glu Ser Asp Arg Ile Ser Ala Met Glu Thr Asn Leu Arg Thr Leu
                    325                 330                 335

Gly Val Gln Thr Asp Val Gly His Asp Trp Met Arg Ile Tyr Pro Ser
                340                 345                 350

Thr Pro His Gly Gly Arg Val Asn Cys His Arg Asp His Arg Ile Ala
                355                 360                 365

Met Ala Phe Ser Ile Leu Gly Leu Arg Val Asp Gly Ile Thr Leu Asp
                370                 375                 380

Asp Pro Gln Cys Val Gly Lys Thr Phe Pro Gly Phe Phe Asp Tyr Leu
    385                 390                 395                 400

Gly Arg Leu Phe Pro Glu Lys Ala Leu Thr Leu Pro Gly
                    405                 410

<210> SEQ ID NO 30
<211> LENGTH: 1244
<212> TYPE: DNA
<213> ORGANISM: Artificial Sequence
<220> FEATURE:
<223> OTHER INFORMATION: grg23(L3P1.F18)
<221> NAME/KEY: CDS
<222> LOCATION: (1)...(1242)

<400> SEQUENCE: 30 atg gaa act gat cgc ctt gtg atc cca gga tcg aaa agc atc acc aac     48
Met Glu Thr Asp Arg Leu Val Ile Pro Gly Ser Lys Ser Ile Thr Asn
  1               5                  10                  15 cgg gct ttg ctt ttg gct gcc gca gcg aag ggc acg tcg gtc ctg gtg     96
Arg Ala Leu Leu Leu Ala Ala Ala Ala Lys Gly Thr Ser Val Leu Val
                 20                  25                  30 aga cca ttg gtc agc gcc gat acc tca gca ttc aaa act gca atc cag    144
Arg Pro Leu Val Ser Ala Asp Thr Ser Ala Phe Lys Thr Ala Ile Gln
             35                  40                  45 gcc ctc ggt gcc aac gtc tca gcc gac ggt gac aat tgg gtc gtt gaa    192
Ala Leu Gly Ala Asn Val Ser Ala Asp Gly Asp Asn Trp Val Val Glu
         50                  55                  60 ggc ctg ggt cag gca ccc cac ctc gac gcc gac atc tgg tgc gag gac    240
Gly Leu Gly Gln Ala Pro His Leu Asp Ala Asp Ile Trp Cys Glu Asp
 65                  70                  75                  80 gca ggt act gtg gcc cgg ttc ctc cct cca ttc gta gcc gca ggt cag    288
Ala Gly Thr Val Ala Arg Phe Leu Pro Pro Phe Val Ala Ala Gly Gln
                 85                  90                  95
```

-continued

```
ggg aag ttc acc gtc gac gga tca gag cag ctg cgg cgg cgc ccg ctt    336
Gly Lys Phe Thr Val Asp Gly Ser Glu Gln Leu Arg Arg Arg Pro Leu
            100                 105                 110 cgg ccc ctg gtc gac ggc atc cgc cac ctg ggc gcc cgc gtc tcc tcc    384
Arg Pro Leu Val Asp Gly Ile Arg His Leu Gly Ala Arg Val Ser Ser
        115                 120                 125 gag cag ctg ccc ctt aca att gaa gcg agc ggg ctg gca ggc ggg gag    432
Glu Gln Leu Pro Leu Thr Ile Glu Ala Ser Gly Leu Ala Gly Gly Glu
    130                 135                 140 tac gaa att gaa gcc cat cag agc agc cag ttc gcc tcc ggc ctg atc    480
Tyr Glu Ile Glu Ala His Gln Ser Ser Gln Phe Ala Ser Gly Leu Ile
145                 150                 155                 160 atg gcc gcc ccg tac gcg aga caa ggc ctg cgt gtg cgg ata cca aat    528
Met Ala Ala Pro Tyr Ala Arg Gln Gly Leu Arg Val Arg Ile Pro Asn
                165                 170                 175 ccc gtg tca cag ccc tac ctc acg atg aca ctg cgg atg atg agg gac    576
Pro Val Ser Gln Pro Tyr Leu Thr Met Thr Leu Arg Met Met Arg Asp
            180                 185                 190 ttc ggc ctt gag acc agc acc gac gga gcc acc gtc agc gtc cct cca    624
Phe Gly Leu Glu Thr Ser Thr Asp Gly Ala Thr Val Ser Val Pro Pro
        195                 200                 205 ggg cgc tac aca gcc cgg cgg tat gaa ata gaa ccg gat gcg tca act    672
Gly Arg Tyr Thr Ala Arg Arg Tyr Glu Ile Glu Pro Asp Ala Ser Thr
    210                 215                 220 gcg tcg tac ttc gcc gcc gct tcc gcc gtc tct ggc agg agc ttc gaa    720
Ala Ser Tyr Phe Ala Ala Ala Ser Ala Val Ser Gly Arg Ser Phe Glu
225                 230                 235                 240 ttt caa ggc ctt ggc aca gac agc atc caa ggc gac acg tca ttc ttc    768
Phe Gln Gly Leu Gly Thr Asp Ser Ile Gln Gly Asp Thr Ser Phe Phe
                245                 250                 255 aat gta ctt ggg cgg ctc ggt gcg gag gtc cac tgg gca ccc aac tcg    816
Asn Val Leu Gly Arg Leu Gly Ala Glu Val His Trp Ala Pro Asn Ser
            260                 265                 270 gtc atc ata tct gga ccg gaa agg ctg aac ggc gac att gaa gtg gat    864
Val Ile Ile Ser Gly Pro Glu Arg Leu Asn Gly Asp Ile Glu Val Asp
        275                 280                 285 atg ggc gag att tcg gac acc ttc atg aca ctc gcg gcg att gcc cct    912
Met Gly Glu Ile Ser Asp Thr Phe Met Thr Leu Ala Ala Ile Ala Pro
    290                 295                 300 ttg gcc gat gga ccc atc acg ata acc aac att ggt cat gca cgg ttg    960
Leu Ala Asp Gly Pro Ile Thr Ile Thr Asn Ile Gly His Ala Arg Leu
305                 310                 315                 320 aag gaa tcc gac cgc atc tca gcg atg gaa acc aac ctg cgc acg ctc   1008
Lys Glu Ser Asp Arg Ile Ser Ala Met Glu Thr Asn Leu Arg Thr Leu
                325                 330                 335 ggt gta caa acc gac gtc gga cac gac tgg atg aga atc tac ccc tct   1056
Gly Val Gln Thr Asp Val Gly His Asp Trp Met Arg Ile Tyr Pro Ser
            340                 345                 350 acc ccg cac ggc ggt aga gtg aat tgc cac cgg gac cac agg atc gct   1104
Thr Pro His Gly Gly Arg Val Asn Cys His Arg Asp His Arg Ile Ala
        355                 360                 365 atg gcg ttt tca atc ctg gga ctg aga gtg gac ggg att acc ctc gac   1152
Met Ala Phe Ser Ile Leu Gly Leu Arg Val Asp Gly Ile Thr Leu Asp
    370                 375                 380 gac cct caa tgc gtc ggg aag acc ttt cct ggc ttc ttc gac tac ctt   1200
Asp Pro Gln Cys Val Gly Lys Thr Phe Pro Gly Phe Phe Asp Tyr Leu
385                 390                 395                 400 gga cgc ctt ttc ccc gaa aag gcg ctt acg ctc ccc ggc tag            1242
Gly Arg Leu Phe Pro Glu Lys Ala Leu Thr Leu Pro Gly  *
```

```
                    405                 410
gg                                                              1244
```

<210> SEQ ID NO 31
<211> LENGTH: 413
<212> TYPE: PRT
<213> ORGANISM: Artificial Sequence
<220> FEATURE:
<223> OTHER INFORMATION: grg23(L3P1.F18)

<400> SEQUENCE: 31

```
Met Glu Thr Asp Arg Leu Val Ile Pro Gly Ser Lys Ser Ile Thr Asn
 1               5                   10                  15

Arg Ala Leu Leu Leu Ala Ala Ala Lys Gly Thr Ser Val Leu Val
             20                  25                  30

Arg Pro Leu Val Ser Ala Asp Thr Ser Ala Phe Lys Thr Ala Ile Gln
         35                  40                  45

Ala Leu Gly Ala Asn Val Ser Asp Gly Asp Asn Trp Val Val Glu
     50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Pro Leu
            100                 105                 110

Arg Pro Leu Val Asp Gly Ile Arg His Leu Gly Ala Arg Val Ser Ser
        115                 120                 125

Glu Gln Leu Pro Leu Thr Ile Glu Ala Ser Gly Leu Ala Gly Gly Glu
    130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Ile Ile Ser Gly Pro Glu Arg Leu Asn Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350
```

```
Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
            405                 410

<210> SEQ ID NO 32
<211> LENGTH: 1244
<212> TYPE: DNA
<213> ORGANISM: Artificial Sequence
<220> FEATURE:
<223> OTHER INFORMATION: grg23(L3P1.O23)
<221> NAME/KEY: CDS
<222> LOCATION: (1)...(1242)

<400> SEQUENCE: 32
```

| | | | | | | | | | | | | | | | | |
|---|---|---|---|---|---|---|---|---|---|---|---|---|---|---|---|---|
| atg | gaa | act | gat | cac | ctt | gtg | atc | cca | gga | tcg | aaa | agc | atc | acc | aac | 48 |
| Met | Glu | Thr | Asp | His | Leu | Val | Ile | Pro | Gly | Ser | Lys | Ser | Ile | Thr | Asn | |
| 1 | | | | 5 | | | | | 10 | | | | | 15 | | |
| cgg | gcg | ttg | ctt | ttg | gct | gcc | gca | gcg | aag | ggc | acg | tcg | gtc | ctg | gtg | 96 |
| Arg | Ala | Leu | Leu | Leu | Ala | Ala | Ala | Ala | Lys | Gly | Thr | Ser | Val | Leu | Val | |
| | | | 20 | | | | | 25 | | | | | 30 | | | |
| aga | cca | ttg | gtc | agc | gcc | gat | acc | tca | gca | ttc | aaa | act | gca | atc | cag | 144 |
| Arg | Pro | Leu | Val | Ser | Ala | Asp | Thr | Ser | Ala | Phe | Lys | Thr | Ala | Ile | Gln | |
| | | 35 | | | | | 40 | | | | | 45 | | | | |
| gcc | ctc | ggt | gcc | aac | gtc | tca | gcc | gac | ggt | gac | aat | tgg | gtc | gtt | gaa | 192 |
| Ala | Leu | Gly | Ala | Asn | Val | Ser | Ala | Asp | Gly | Asp | Asn | Trp | Val | Val | Glu | |
| | 50 | | | | | 55 | | | | | 60 | | | | | |
| ggc | ttg | ggt | cag | gca | ccc | cac | ctc | gac | gcc | gac | atc | tgg | tgc | gag | gac | 240 |
| Gly | Leu | Gly | Gln | Ala | Pro | His | Leu | Asp | Ala | Asp | Ile | Trp | Cys | Glu | Asp | |
| 65 | | | | | 70 | | | | | 75 | | | | | 80 | |
| gca | ggt | act | gtg | gcc | cgg | ttc | ctc | cct | cca | ttc | gta | gcc | gca | ggt | cag | 288 |
| Ala | Gly | Thr | Val | Ala | Arg | Phe | Leu | Pro | Pro | Phe | Val | Ala | Ala | Gly | Gln | |
| | | | | 85 | | | | | 90 | | | | | 95 | | |
| ggg | aag | ttc | acc | gtc | gac | gga | tca | gag | cag | ctg | cgg | cgg | cgc | ccg | ctt | 336 |
| Gly | Lys | Phe | Thr | Val | Asp | Gly | Ser | Glu | Gln | Leu | Arg | Arg | Arg | Pro | Leu | |
| | | | 100 | | | | | 105 | | | | | 110 | | | |
| cgg | ccc | ctg | gtc | gac | ggc | atc | cgc | cac | ctg | ggc | gcc | cgc | gtc | tcc | tcc | 384 |
| Arg | Pro | Leu | Val | Asp | Gly | Ile | Arg | His | Leu | Gly | Ala | Arg | Val | Ser | Ser | |
| | | 115 | | | | | 120 | | | | | 125 | | | | |
| gag | cag | ctg | ccc | ctt | aca | att | gaa | gcg | agc | ggg | ctg | gca | ggc | ggg | gag | 432 |
| Glu | Gln | Leu | Pro | Leu | Thr | Ile | Glu | Ala | Ser | Gly | Leu | Ala | Gly | Gly | Glu | |
| | 130 | | | | | 135 | | | | | 140 | | | | | |
| tac | gaa | att | gaa | gcc | cat | cag | agc | agc | cag | ttc | gcc | tcc | ggc | ctg | atc | 480 |
| Tyr | Glu | Ile | Glu | Ala | His | Gln | Ser | Ser | Gln | Phe | Ala | Ser | Gly | Leu | Ile | |
| 145 | | | | | 150 | | | | | 155 | | | | | 160 | |
| atg | gcc | gcc | ccg | tac | gcg | aga | caa | ggc | ctg | cgt | gtg | cgg | ata | cca | aat | 528 |
| Met | Ala | Ala | Pro | Tyr | Ala | Arg | Gln | Gly | Leu | Arg | Val | Arg | Ile | Pro | Asn | |
| | | | | 165 | | | | | 170 | | | | | 175 | | |
| ccc | gtg | tca | cag | ccc | tac | ctc | acg | atg | aca | ctg | cgg | atg | atg | agg | gac | 576 |
| Pro | Val | Ser | Gln | Pro | Tyr | Leu | Thr | Met | Thr | Leu | Arg | Met | Met | Arg | Asp | |
| | | | 180 | | | | | 185 | | | | | 190 | | | |
| ttc | ggc | ctt | gag | acc | agc | acc | gac | gga | gcc | acc | gtc | agc | gtc | cct | cca | 624 |
| Phe | Gly | Leu | Glu | Thr | Ser | Thr | Asp | Gly | Ala | Thr | Val | Ser | Val | Pro | Pro | |
| | | 195 | | | | | 200 | | | | | 205 | | | | |
| ggg | cgc | tac | aca | gcc | cgg | cgg | tat | gaa | ata | gaa | ccg | gat | gcg | tca | act | 672 |
| Gly | Arg | Tyr | Thr | Ala | Arg | Arg | Tyr | Glu | Ile | Glu | Pro | Asp | Ala | Ser | Thr | |

-continued

| | | |
|---|---|---|
| gcg tcg tac ttc gcc gcc gct tcc gcc gtc tct ggc agg agc ttc gaa<br>Ala Ser Tyr Phe Ala Ala Ala Ser Ala Val Ser Gly Arg Ser Phe Glu<br>225                     230                     235                     240 | 720 |
| ttt caa ggc ctt ggc aca gac agc atc caa ggc gac acg tca ttt ttc<br>Phe Gln Gly Leu Gly Thr Asp Ser Ile Gln Gly Asp Thr Ser Phe Phe<br>245                     250                     255 | 768 |
| aat gta ctt ggg cgg ctc ggt gcg gag gtc cac tgg gca ccc aac tcg<br>Asn Val Leu Gly Arg Leu Gly Ala Glu Val His Trp Ala Pro Asn Ser<br>260                     265                     270 | 816 |
| gtc acc ata tct gga ccg gaa agg ctg aac ggc gac att gaa gtg gat<br>Val Thr Ile Ser Gly Pro Glu Arg Leu Asn Gly Asp Ile Glu Val Asp<br>275                     280                     285 | 864 |
| atg ggc gag att tcg gac acc ttc atg aca ctc gcg gcg att gcc cct<br>Met Gly Glu Ile Ser Asp Thr Phe Met Thr Leu Ala Ala Ile Ala Pro<br>290                     295                     300 | 912 |
| ttg gcc gat gga ccc atc acg ata acc aac att ggt cat gca cgg ttg<br>Leu Ala Asp Gly Pro Ile Thr Ile Thr Asn Ile Gly His Ala Arg Leu<br>305                     310                     315                     320 | 960 |
| aag gaa tcc gac cgc atc tca gcg atg gaa acc aac ctg cgc acg ctc<br>Lys Glu Ser Asp Arg Ile Ser Ala Met Glu Thr Asn Leu Arg Thr Leu<br>                     325                     330                     335 | 1008 |
| ggt gta caa acc gac gtc gga cac gac tgg atg aga atc tac ccc tct<br>Gly Val Gln Thr Asp Val Gly His Asp Trp Met Arg Ile Tyr Pro Ser<br>                     340                     345                     350 | 1056 |
| acc ccg cac ggc ggt aga gtg aat tgc cac cgg gac cac agg atc gct<br>Thr Pro His Gly Gly Arg Val Asn Cys His Arg Asp His Arg Ile Ala<br>                     355                     360                     365 | 1104 |
| atg gcg ttt tca atc ctg gga ctg aga gtg gac ggg att acc ctc gac<br>Met Ala Phe Ser Ile Leu Gly Leu Arg Val Asp Gly Ile Thr Leu Asp<br>370                     375                     380 | 1152 |
| gac cct caa tgc gtc ggg aag acc ttt cct ggc ttc ttc gac tac ctt<br>Asp Pro Gln Cys Val Gly Lys Thr Phe Pro Gly Phe Phe Asp Tyr Leu<br>385                     390                     395                     400 | 1200 |
| gga cgc ctt ttc ccc gaa aag gcg ctt acg ctt ccc ggc tag<br>Gly Arg Leu Phe Pro Glu Lys Ala Leu Thr Leu Pro Gly *<br>                     405                     410 | 1242 |
| gg | 1244 |

```
<210> SEQ ID NO 33
<211> LENGTH: 413
<212> TYPE: PRT
<213> ORGANISM: Artificial Sequence
<220> FEATURE:
<223> OTHER INFORMATION: grg23(L3P1.023)

<400> SEQUENCE: 33
```

Met Glu Thr Asp His Leu Val Ile Pro Gly Ser Lys Ser Ile Thr Asn
 1               5                  10                  15

Arg Ala Leu Leu Leu Ala Ala Ala Lys Gly Thr Ser Val Leu Val
             20                  25                  30

Arg Pro Leu Val Ser Ala Asp Thr Ser Ala Phe Lys Thr Ala Ile Gln
         35                  40                  45

Ala Leu Gly Ala Asn Val Ser Ala Asp Gly Asp Asn Trp Val Val Glu
     50                  55                  60

Gly Leu Gly Gln Ala Pro His Leu Asp Ala Asp Ile Trp Cys Glu Asp
 65                  70                  75                  80

Ala Gly Thr Val Ala Arg Phe Leu Pro Pro Phe Val Ala Ala Gly Gln
                 85                  90                  95

Gly Lys Phe Thr Val Asp Gly Ser Glu Gln Leu Arg Arg Pro Leu
        100                 105                 110

Arg Pro Leu Val Asp Gly Ile Arg His Leu Gly Ala Arg Val Ser Ser
    115                 120                 125

Glu Gln Leu Pro Leu Thr Ile Glu Ala Ser Gly Leu Ala Gly Gly Glu
130                 135                 140

Tyr Glu Ile Glu Ala His Gln Ser Ser Gln Phe Ala Ser Gly Leu Ile
145                 150                 155                 160

Met Ala Ala Pro Tyr Ala Arg Gln Gly Leu Arg Val Arg Ile Pro Asn
                165                 170                 175

Pro Val Ser Gln Pro Tyr Leu Thr Met Thr Leu Arg Met Met Arg Asp
            180                 185                 190

Phe Gly Leu Glu Thr Ser Thr Asp Gly Ala Thr Val Ser Val Pro Pro
        195                 200                 205

Gly Arg Tyr Thr Ala Arg Arg Tyr Glu Ile Glu Pro Asp Ala Ser Thr
    210                 215                 220

Ala Ser Tyr Phe Ala Ala Ala Ser Ala Val Ser Gly Arg Ser Phe Glu
225                 230                 235                 240

Phe Gln Gly Leu Gly Thr Asp Ser Ile Gln Gly Asp Thr Ser Phe Phe
                245                 250                 255

Asn Val Leu Gly Arg Leu Gly Ala Glu Val His Trp Ala Pro Asn Ser
            260                 265                 270

Val Thr Ile Ser Gly Pro Glu Arg Leu Asn Gly Asp Ile Glu Val Asp
        275                 280                 285

Met Gly Glu Ile Ser Asp Thr Phe Met Thr Leu Ala Ala Ile Ala Pro
    290                 295                 300

Leu Ala Asp Gly Pro Ile Thr Ile Thr Asn Ile Gly His Ala Arg Leu
305                 310                 315                 320

Lys Glu Ser Asp Arg Ile Ser Ala Met Glu Thr Asn Leu Arg Thr Leu
                325                 330                 335

Gly Val Gln Thr Asp Val Gly His Asp Trp Met Arg Ile Tyr Pro Ser
            340                 345                 350

Thr Pro His Gly Gly Arg Val Asn Cys His Arg Asp His Arg Ile Ala
        355                 360                 365

Met Ala Phe Ser Ile Leu Gly Leu Arg Val Asp Gly Ile Thr Leu Asp
    370                 375                 380

Asp Pro Gln Cys Val Gly Lys Thr Phe Pro Gly Phe Phe Asp Tyr Leu
385                 390                 395                 400

Gly Arg Leu Phe Pro Glu Lys Ala Leu Thr Leu Pro Gly
                405                 410

<210> SEQ ID NO 34
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 34
cagggatccg gcatggaaac tgatcgacta gtg                              33

<210> SEQ ID NO 35
<211> LENGTH: 29
<212> TYPE: DNA
<213> ORGANISM: Artificial Sequence
<220> FEATURE:

```
<223> OTHER INFORMATION: oligonucleotide primer

<400> SEQUENCE: 35
attggcgcgc cctagccggg gagcgtaag                                            29

<210> SEQ ID NO 36
<211> LENGTH: 11
<212> TYPE: PRT
<213> ORGANISM: Artificial Sequence
<220> FEATURE:
<223> OTHER INFORMATION: polyhistidine tag

<400> SEQUENCE: 36

Met Ala His His His His His His Gly Ser Gly
 1               5                  10
```

GRG23 AND GRG51 GENES CONFERRING HERBICIDE RESISTANCE

CROSS REFERENCE TO RELATED APPLICATION

This application claims the benefit of U.S. Provisional Application Ser. Nos. 60/741,166, filed Dec. 1, 2005, and 60/817,799, filed Jun. 30, 2006, the contents of which are incorporated in their entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "320069_ReplacementSequenceListing.txt", created on Jun. 12, 2009, and having a size of 141 kilobytes and is filed as an Amendment to the specification on Jun. 15, 2009. The sequence listing contained in this ASCII formatted document is part of the specification and is herein incorporated by reference in its entirety.

FIELD OF THE INVENTION

This invention provides novel genes encoding herbicide resistance, which are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid (S3P) to 5-enolpyruvyl-3-phosphoshikimic acid. Inhibition of this enzyme (5-enolpyruvylshikimate-3-phosphate synthase; referred to herein as "EPSPS") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945). However, there is a need for other herbicide resistance genes.

EPSPS kinetic activity can be assayed by measuring the liberation of phosphate. Phosphate liberation is detected using a coupled assay for the fluorescent detection of phosphate based on the generation of N-acetyl-3,7-dihydroxyphenoxacine (Amplex® Red), as is known in the art (Vazquez et al. (2003) *Analytical Biochemistry* 320: 292-298). The published assay conditions can lead to saturation of the assay in experiments where phosphate is liberated very quickly. Additional methods are needed for the measurement of EPSPS kinetic activity.

SUMMARY OF INVENTION

Compositions and methods for conferring herbicide resistance or tolerance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. Compositions also include antibodies to the herbicide resistance or tolerance polypeptides. As noted, the nucleotide sequences of the invention can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

Isolated nucleic acid molecules and variants thereof encoding herbicide resistance or tolerance polypeptides are provided. Additionally, amino acid sequences and variants thereof encoded by the polynucleotides that confer herbicide resistance or tolerance are encompassed. The present invention provides for isolated nucleic acid molecules comprising a nucleotide sequence set forth in SEQ ID NO:1, 3, or 5, a nucleotide sequence encoding the amino acid sequence set forth in SEQ ID NO:2, 4, or 6, the herbicide resistance nucleotide sequence deposited in a bacterial host as Accession Nos. NRRL B-30888 or NRRL B-30949, as well as variants and fragments thereof. Nucleotide sequences that are complementary to a nucleotide sequence of the invention, or that hybridize to a sequence of the invention are also encompassed.

Methods for measuring enzyme kinetic activity using fluorogenic substrates are also provided.

DESCRIPTION OF FIGURES

FIG. 1 shows an alignment of the GRG23 ORF1 amino acid sequence (SEQ ID NO:2) and GRG51 (SEQ ID NO:6) with *Bacillus clausii* (SEQ ID NO:7), *Rubrobacer xylanophilus* (SEQ ID NO:8), *Escherichia coli* (SEQ ID NO: 11), *Agrobacterium* sp. strain CP4 (SEQ ID NO:10) and *Zea mays* (SEQ ID NO:9).

DETAILED DESCRIPTION

Figure 2:
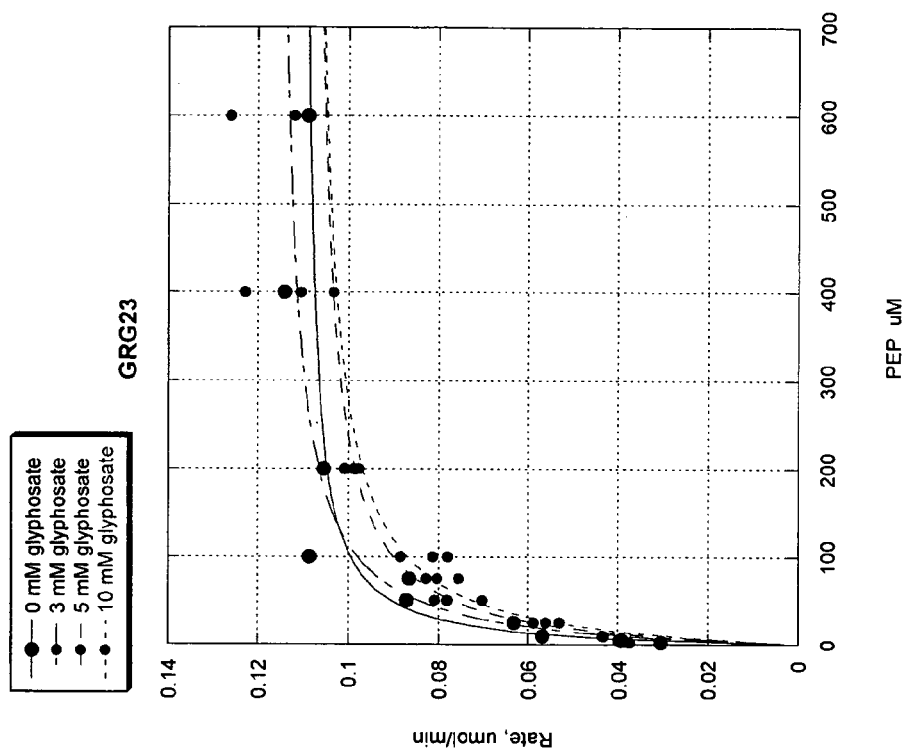
FIG. 2 shows a scatter plot of GRG23 enzyme activity (y axis) as a function of the concentration of PEP (x axis) at glyphosate concentrations of 0, 3, 5 and 10 mM.
Figure 3:
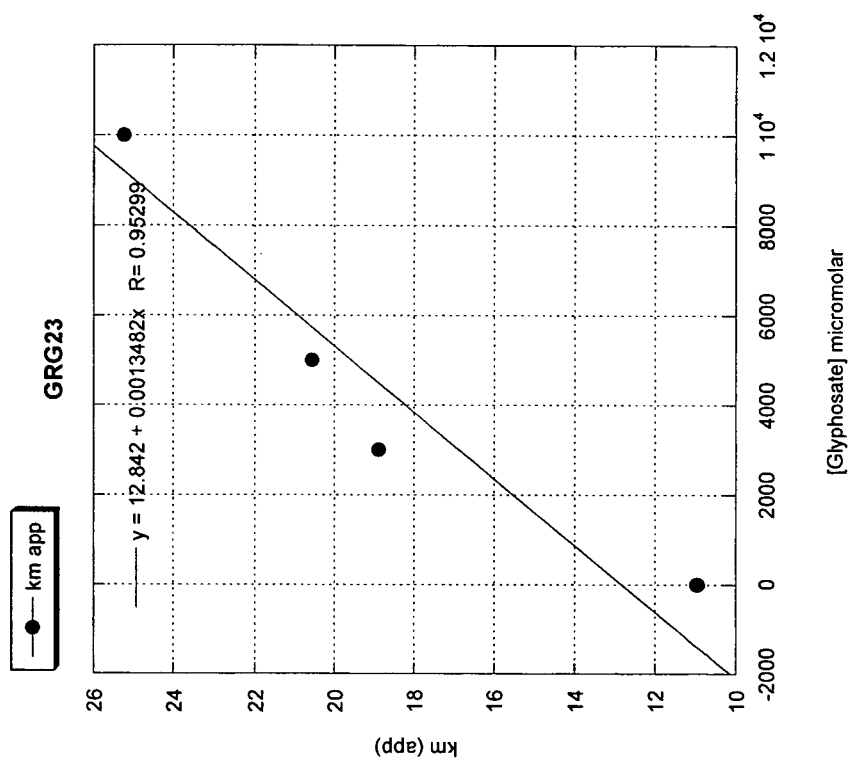
FIG. 3 shows a scatter plot of $K_m$ (app) (y axis) as a function of glyphosate concentration (x axis). The −X intercept represents the $K_i$ for glyphosate.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is drawn to compositions and methods for regulating herbicide resistance in organisms, particularly in plants or plant cells. The methods involve transforming organisms with nucleotide sequences encoding the glyphosate resistance gene of the invention. The nucleotide sequences of the invention are useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. Nucleotide sequences of the glyphosate resistance gene (grg23 and grg51) and the amino acid sequences of the proteins encoded thereby are disclosed. The sequences find use in the construction of expression vectors for subsequent transformation into plants of interest, as probes for the isolation of other glyphosate resistance genes, as selectable markers, and the like. Thus, by "glyphosate resistance gene of the invention is intended the nucleotide sequence set forth in SEQ ID NO:1 or 3, and variants and fragments thereof (SEQ ID NO:5, 12, 14, 16, 18, 20, 22, 24, 26, 28, 30, and 32), that encode a glyphosate resistance or tolerance polypeptide. Likewise, a "glyphosate resistance polypeptide of the invention" is a polypeptide having the amino acid sequence set forth in SEQ ID NO:2 or 4, and variants and fragments thereof (SEQ ID NO:6, 15, 17, 19, 21, 23, 25, 27, 29, 31, and 33), that confer glyphosate resistance or tolerance to a host cell.

Plasmids containing the herbicide resistance nucleotide sequences of the invention were deposited in the permanent collection of the Agricultural Research Service Culture Collection, Northern Regional Research Laboratory (NRRL) on Nov. 18, 2005, and assigned Accession No. NRRL B-30888 (grg23), and on Jun. 26, 2006 and assigned Accession No. NRRL B-30949 (grg51). This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the ATCC. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

Nucleotide sequences encoding the proteins of the present invention include the sequences set forth in SEQ ID NO:1, 3, and 5 the herbicide resistance nucleotide sequence deposited in a bacterial host as Accession Nos. NRRL B-30888 and NRRL B-30949, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the herbicide resistance protein encoded by these nucleotide sequences is set forth in SEQ ID NO:2, 4, or 6. The invention also encompasses nucleic acid molecules comprising nucleotide sequences encoding partial-length herbicide resistance proteins, and complements thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of the nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 contiguous nucleotides, or up to the number of nucleotides present in a full-length herbicide resistance-encoding nucleotide sequence disclosed herein (for example, 1892 nucleotides for SEQ ID NO:1, 1259 nucleotides for SEQ ID NO:3, and 1242 nucleotides for SEQ ID NO:5). By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance proteins disclosed herein as SEQ ID NO:2, 4, or 6. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400 contiguous amino acids, or up to the total number of amino acids present in a full-length herbicide resistance protein of the invention (for example, 436 amino acids for SEQ ID NO:2, 413 amino acids for SEQ ID NO:4, and 413 amino acids for SEQ ID NO:6).

Herbicide resistance proteins of the present invention are encoded by a nucleotide sequence sufficiently identical to the nucleotide sequence of SEQ ID NO:1, 3, or 5. The term "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403-410. BLAST nucleotide searches can be performed with the BLASTN program, score=100, wordlength=12, to obtain nucleotide sequences homologous to GDC-like nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., San Diego, Calif.). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode the herbicide resistance protein disclosed herein but that differ conservatively because of the degeneracy of the genetic code, as well as those that are sufficiently identical as discussed above (for example, SEQ ID NO:5, 12, 14, 16, 18, 20, 22, 24, 26, 28, 30, and 32 are variants of SEQ ID NO:1). Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues.

Lys-22, Arg-124, Asp-313, Arg-344, Arg-386, and Lys-411, are conserved residues of the EPSP synthase from *E. coli* (Schönbrunn et al. (2001) *Proc. Natl. Acad. Sci. USA* 98:1376-1380). Conserved residues important for EPSP synthase activity also include Arg-100, Asp-242, and Asp-384 (Selvapandiyan et al. (1995) *FEBS Letters* 374:253-256). Arg-27 binds to S3P (Shuttleworth et al. (1999) *Biochemistry* 38:296-302).

Alternatively, variant nucleotide sequences can be made by introducing mutations randomly along all or part of the coding sequence, such as by saturation mutagenesis, and the resultant mutants can be screened for the ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like corresponding herbicide resistance sequences can be identified, such sequences having substantial identity to the sequences of the invention. See, for example, Sambrook and Russell (2001) *Molecular Cloning: A Laboratory Manual* (Cold Spring Harbor Laboratory Press, Cold Spring Harbor, N.Y.) and Innis, et al. (1990) *PCR Protocols: A Guide to Methods and Applications* (Academic Press, St. Louis, Mo.).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell (2001) supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence(s) disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, 400, 500, 600, 700, 800, 900, 1000, 1200, 1400, 1600, or 1800 consecutive nucleotides of herbicide resistance-encoding nucleotide sequence(s) of the invention or a fragment or variant thereof. Methods for the preparation of probes for hybridization are generally known in the art and are disclosed in Sambrook and Russell (2001) supra, and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, and at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than about 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 11° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" or "herbicide tolerance protein" is intended a protein having the amino acid sequence set forth in SEQ ID NO:2, 4, or 6. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth in SEQ ID NO:2, 4, or 6 and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188, 642, each of which are herein incorporated by reference in their entirety. As used here, a fragment comprises at least 8 contiguous amino acids of SEQ ID NO: 2, 4, or 6. The invention encompasses other fragments, however, such as any fragment in the protein greater than about 10, 20, 30, 50, 100, 150, 200, 250, 300, 350, or 400 amino acids.

By "variants" is intended proteins or polypeptides having an amino acid sequence that is at least about 60%, 65%, at least about 70%, 75%, at least about 80%, 85%, 90%, 91%, 92%, 93%, 94%, 95%, 96%, 97%, 98% or 99% identical to the amino acid sequence of SEQ ID NO:2, 4, or 6 (for example, SEQ ID NO:6, 15, 17, 19, 21, 23, 25, 27, 29, 31, and 33 are variants of SEQ ID NO:2). Variants also include polypeptides encoded by a nucleic acid molecule that hybridizes to the nucleic acid molecule of SEQ ID NO:1, 3, or 5, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188, 642, each of which are herein incorporated by reference in their entirety.

Bacterial genes, such as the grg23 or grg51 gene of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of grg23 or grg51 that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies. A Laboratory Manual* (Cold Spring Harbor Laboratory, Cold Spring Harbor, N.Y.); U.S. Pat. No. 4,196,265).

Altered or Improved Variants

It is recognized that the DNA sequence of grg23 or grg51 may be altered by various methods, and that these alterations may result in DNA sequences encoding proteins with amino acid sequences different than that encoded by grg23 or grg51. This protein may be altered in various ways including amino acid substitutions, deletions, truncations, and insertions. Methods for such manipulations are generally known in the art. For example, amino acid sequence variants of the GRG23 or GRG51 protein can be prepared by mutations in the DNA. This may also be accomplished by one of several forms of mutagenesis and/or by directed evolution. In some aspects, the changes encoded in the amino acid sequence will not substantially affect the function of the protein. Such variants will possess the desired herbicide resistance activity. However, it is understood that the ability of GRG23 or GRG51 to confer herbicide resistance may be improved by use of such techniques upon the compositions of the present invention. For example, GRG23 or GRG51 may be expressed in host cells that exhibit high rates of base misincorporation during DNA replication, such as XL-1 Red (Stratagene, La Jolla, Calif.). After propagation in such strains, grg23 or grg51 DNA can be isolated (for example by preparing plasmid DNA, or by amplifying by PCR and cloning the resulting PCR fragment into a vector) and cultured in non-mutagenic strains. Clones containing mutations in grg23 or grg51 can be identified by measuring improved resistance to an herbicide such as glyphosate, for example by growing cells in increasing concentrations of glyphosate and testing for clones that confer tolerance to increasing concentrations of glyphosate.

Alternatively, alterations may be made to the protein sequence of many proteins at the amino or carboxy terminus without substantially affecting activity. These alterations can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest; (2) introduce a binding domain, enzymatic activity, or epitope to facilitate either protein purification, protein detection, or other experimental uses known in the art; or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

Provided herein are novel isolated genes that confer resistance to an herbicide. Also provided are an amino acid sequences of the GRG23 and GRG51 proteins. The protein resulting from translation of this gene allows cells to function in the presence of concentrations of an herbicide that are otherwise toxic to cells including plant cells and bacterial cells.

In one aspect of the invention, the grg23 or grg51 gene is useful as a marker to assess transformation of bacterial or plant cells.

By engineering grg23 or grg51 to be (1) expressed from a bacterial promoter known to stimulate transcription in the organism to be tested, (2) properly translated to generate an intact GRG23 or GRG51 peptide, and (3) placing the cells in an otherwise toxic concentration of herbicide, cells that have been transformed with DNA by virtue of their resistance to herbicide can be identified. By "promoter" is intended a nucleic acid sequence that functions to direct transcription of a downstream coding sequence. The promoter, together with other transcriptional and translational regulatory nucleic acid sequences, (also termed "control sequences") are necessary for the expression of a DNA sequence of interest.

Transformation of bacterial cells is accomplished by one of several techniques known in the art, including but not limited to, electroporation or chemical transformation (See, for example, Ausubel (ed.) (1994) *Current Protocols in Molecular Biology* (John Wiley and Sons, Inc., Indianapolis, Ind.)). Markers conferring resistance to toxic substances are useful in identifying transformed cells (having taken up and expressed the test DNA) from non-transformed cells (those not containing or not expressing the test DNA). In one aspect of the invention, the grg23 or grg51 gene is useful as a marker to assess transformation of bacterial or plant cells.

Transformation of plant cells can be accomplished in a similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants, cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The grg23 or grg51 gene of the invention may be modified to obtain or enhance expression in plant cells. The herbicide resistance sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a translational and transcriptional termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this transport typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. The plant expression cassette can also be engineered to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92: 1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Measurement of EPSPS Activity

In one embodiment of the present invention, the glyphosate-resistant EPSPS enzyme has a $K_m$ for phosphoenolpyruvate (PEP) between about 1 and about 150 uM, including about 2 uM, about 3, 4, 5, 6, 7, 8, 9, 10, 20, 30, 40, 50, 60, 70, 80, 90, 100, 110, 120, 130 or about 140 uM, and a $K_i$ (glyphosate)/$K_m$ (PEP) between about 500 and about 1000, about 550, about 600, 650, 700, 750, 800, 850, 900, 950, or up to about 1000. As used herein, $K_m$ and $K_i$ are measured under conditions in which the enzyme obeys Michaelis-Menten kinetics, around pH 7. One nonlimiting measurement technique uses the enzyme in purified form in potassium chloride and HEPES buffer at pH 7 at room temperature and uses concentrations of glyphosate from 0 to 10 mM.

EPSPS kinetic activity can be assayed, for example, by measuring the liberation of phosphate that results during the catalysis of a substrate of EPSPS (for example, PEP and S3P) to its subsequent reaction product (for example, 5-enolpyruvyl-3-phosphoshikimic acid) using a fluorescent assay described by Vazquez et al. (2003) *Anal. Biochem.* 320(2): 292-298. This assay is based on the oxidation of the non-fluorescent compound N-acetyl-3,7-dihydroxyphenoxacine (Amplex® Red, Invitrogen, Carlsbad, Calif.) to the fluorescent compound resorufin by hydrogen peroxide (Zhou and Panchuk-Voloshina (1997) *Anal. Biochem.* 253:169-174). The reaction relies on the utilization of phosphate by purine nucleoside phosphorylase (PNP), xanthine oxidase (XOD), and horseradish peroxidase (HRP). Phosphate liberation is linked to the level of fluorescence that results from the conversion of Amplex® Red to resorufin. Fluorescence can be measured, for example, using a filter fluorometer, plate reader, spectrofluorometer, spectrophotometer, or the like, using methods well known in the art. The fluorescence generated by the reaction can be detected using a fluorometer set for excitation in the range of about 530 to about 560 nm and an emission of about 590 nm. Absorbance can be detected (for example, using a spectrophotometer or plate reader) at about 565 nm.

In one embodiment, the present invention encompasses an alteration of the previously reported assay conditions to extend the dynamic range of the assay to accommodate a wider range of substrate concentrations. The alteration comprises a concentration of XOD of at least 1 U/ml, about 1 to about 1.25 U/ml, about 1.25 to about 1.5 U/ml, about 1.5 to about 2 U/ml, or greater than 2 U/ml; a concentration of PNP greater than 0.1 U/ml, about 0.1 to about 0.5 U/ml, about 0.5 to about 1 U/ml, about 1 to about 1.5 U/ml, about 1.5 to about 2 U/ml, or greater than 2 U/ml; and a concentration of Amplex® Red greater than 100 µM, about 100 to about 200 µM, about 200 to about 300 µM, about 300 to about 400 µM, about 400 to about 500 µM, about 500 to about 600 µM, about 700 to about 800 µM, about 800 to about 900 µM, about 900 to about 1000 µM, or greater than about 1000 µM. This modification can be applied to assays measuring the kinetic activity of any enzyme in which phosphate is liberated during a reaction catalyzed by the enzyme.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassaya, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by grg23 or grg51 is then tested by hybridizing the filter to a radioactive probe derived from a GDC by methods known in the art (Sambrook and Russell (2001) supra)

Western blot and biochemical assays and the like may be carried out on the transgenic plants to determine the presence of protein encoded by the herbicide resistance gene by standard procedures (Sambrook and Russell (2001) supra) using antibodies that bind to one or more epitopes present on the herbicide resistance protein.

The following examples are offered by way of illustration and not by way of limitation.

EXPERIMENTAL

Example 1

Isolation of ATX21308

ATX 21308 was isolated by plating samples of soil on Enriched Minimal Media 3 (EMM3) containing phosphates and 50 mM glyphosate. Since EMM3 contains no aromatic amino acids, a strain must be resistant to glyphosate in order to grow on this media.

Approximately one gram of soil is suspended in approximately 10 ml of water, and mixed in a vortex mixer for 5 seconds. 100 µl of this suspension is added to 1 ml of EMM3 with phosphate but no glyphosate. EMM3 contains (per liter, pH 7.0): 10 g sucrose, 1 g NH$_4$Cl, 0.2 g MgSO$_4$.7H$_2$O, 0.01 g FeSO$_4$.7H$_2$O, 0.007 g MnSO$_4$.H$_2$O and 10 ml of phosphate solution containing (per liter, pH 7.0) 210 g Na$_2$HPO$_4$ and 90 g NaH$_2$PO$_4$. The culture is shaken on a tissue culture roller drum at 21° C. overnight and then plated onto EMM3 agar containing 50 mM glyphosate. After three days, the isolate is plated onto Luria Bertani (LB) agar to confirm single morphology. After six days, a single colony is streaked onto EMM3 agar containing 50 mM glyphosate. The isolate grew overnight on 50 mM glyphosate plates. One particular strain, designated ATX21308, was selected due to its ability to grow in the presence of high glyphosate concentrations. This strain is tested for its ability to grow in the presence of glyphosate in liquid culture and is capable of growing up to approximately 300 mM glyphosate under the conditions tested.

Example 2

Preparation and Screening of Cosmid Libraries

Total DNA was extracted from a culture of ATX21308 using methods commonly known in the art. The DNA was partially digested with restriction enzyme Sau3A1 and ligated with SuperCos (Stratagene) vector fragment according to the manufacturer's directions. Ligation products were packaged into phage particles using GigaPack III XL packaging extract (Stratagene), transfected into *E. coli* cells, and plated on LB Agar containing 50 µg/ml kanamycin to select for colonies containing cosmids.

Individual colonies were picked into 384-well plates containing LB broth and 50 µg/ml kanamycin, and grown to saturation. Cells from these cultures were diluted 1:10, then pinned onto M63 agar plates containing 50 µg/ml kanamycin, and either 0 mM, 10 mM, 20 mM, or 50 mM glyphosate. [M63 agar medium 100 mM $KH_2PO_4$, 15 mM $(NH_4)_2SO_4$, 50 µM $CaCl_2$, 1 µM $FeSO_4$, 50 µM $MgCl_2$, 55 mM glucose, 25 mg/liter L-proline, 10 mg/liter thiamine HCl, sufficient NaOH to adjust the pH to 7.0, and 15 g/liter agar]. Transformants that grow more rapidly at the higher glyphosate concentrations were isolated and digested with restriction enzyme EcoR I to identify cosmids with shared restriction patterns. Several clones which grew in the presence of glyphosate and share similar EcoR I restriction patterns were identified. One of these cosmid clones, pAX1924, was selected for further experiments.

Example 3

Identification of grg23 in Cosmid pAX1924

To identify the gene(s) responsible for the glyphosate resistance shown by cosmid pAX1924, DNA from this clone is mutagenized with transposable elements. In this method, clones that have suffered transposon insertions and have lost the ability to confer glyphosate resistance are identified. The location of the transposon insertions identifies the open reading frame responsible for the glyphosate resistance phenotype.

Cosmid pAX1924 is subjected to in vitro transposon mutagenesis using an EZ::TN Insertion Kit (Epicentre, Madison, Wis.) according to the manufacturer's protocol. This process randomly inserts a transposon fragment into the cosmid DNA and thus randomly disrupts the function of genes in the cosmid. This particular transposon contains a gene encoding resistance to trimethoprim, so transposon insertion clones may be selected by the ability to grow in the presence of that antibiotic. The locations of the transposon insertions may be determined by restriction fragment mapping or by sequencing with primers that anneal in the transposon. Transposon insertion clones of pAX1924 are plated on M63 medium containing glyphosate. Multiple transposon-containing clones are identified which have lost the ability to grow in the presence of glyphosate, indicating that the transposon has disrupted the gene responsible for resistance.

The DNA sequence is determined for the region of pAX1924 containing the transposon insertions using sequencing methods well known in the art. Using this sequence information, DNA primers are synthesized and utilized to determine the DNA sequence of pAX1924 in the region encompassing the transposon insertions. Analysis of the resulting DNA sequence shows that this region contains a single gene. This gene is designated herein as grg23. Analysis of grg23 shows that it is capable of yielding two possible proteins in bacterial cells due to the presence of potential alternate translational start sites. The first ORF (ORF1) initiates with a GTG start codon at positions 109-111 of SEQ ID NO:1, and ends at a TAG stop codon at nucleotides 1417-1419 of SEQ ID NO:1. The second ORF (ORF2) starts at an ATG start codon at nucleotides 178-180 of SEQ ID NO:1, and ends at the TAG stop codon at nucleotides 1417-1419 of SEQ ID NO: 1. Translation of ORF1 yields the amino acid sequence set forth in SEQ ID NO:2. Translation of ORF2 yields the amino acid sequence set forth in SEQ ID NO:4.

Analysis of the DNA region surrounding grg23 suggests that ORF2 is preceded by a ribosome binding site, whereas there is no obvious ribosome binding site preceding the ORF1 translation start. Furthermore, alignment of both open reading frames with representative EPSPS enzymes shows that few EPSPS enzymes contain this N-terminal extension encoded within ORF1. Thus, the functional ORF encoded by grg23 in bacteria is ORF2. Therefore, as used herein, GRG23 refers to that which is encoded by ORF2 (nucleotides 178-1419 of SEQ ID NO:1). Nonetheless, it is well known in the art that EPSPS enzymes are quite tolerant of additional amino acids at their N-terminus. Therefore, expression of ORF1 (nucleotides 109-1419 of SEQ ID NO:1) should also yield an EPSPS that confers glyphosate resistance.

To test the ability of ORF2 to function as an EPSPS and confer glyphosate resistance upon cells, this open reading frame can be subcloned and expressed in *E. coli*.

Example 4

Subcloning of grg23 into Vectors for Expression in *E. coli*

The gene encoding GRG23 ORF2 (starting with ATG (positions 178-180 of SEQ ID NO:1), expressing a 413 amino acid protein) was subcloned into pUC18 and pRSF1b using the same cloning strategy outlined above. A PCR primer [5' CAGGGATCCGGCATGGAAACTGATCGACTAGTG 3' (SEQ ID NO:34)] was synthesized that adds a BamHI site followed by GGC (5'-GGATCCGGC-3', residues 2-10 of SEQ ID NO:34) immediately 5' of the start site. A $2^{nd}$ primer was synthesized [5' ATTGGCGCGCCCTAGCCGGG-GAGCGTAAG 3' (SEQ ID NO:35)] that added an AscI site immediately 3' of the stop sequence (5'-GGCGCGCC-3') (residues 3-10 of SEQ ID NO:35). The grg23 coding region is amplified by PCR using PFUULTRA™ DNA polymerase (Stratagene). Following PCR amplification of grg23 using these primers and restriction digestion with BamH I/AscI, the PCR product was ligated into pUC 19 (digested with BamHI and AscI)and pRSF1b (digested with BamHI and AscI), and insert-containing colonies were obtained. The pUC 18-grg23 clone (designated herein as pAX1927) was confirmed by restriction digestion and by DNA sequencing.

Similarly, the expression vector pAX1909 was digested with BamHI and AscI, and the vector containing the fragment was gel-purified by methods well known in the art. pAX1909 is a derivative of PRSF-1b (Novagen, San Diego, Calif.), modified to contain a BamHI site directly 3' of the region encoding the histidine rich "His-Tag." Thus, proteins cloned into pAX1909 are in-frame fusions that contain the additional amino acids MAHHHHHHGSG (SEQ ID NO: 36). Vectors such as pAX1909 are typically developed for protein expression and purification, and these methods are well known in the art.

The digested PCR product resulting above was ligated into the digested pAX1909 vector, and insert-containing colonies were obtained. The pAX1909-grg23 clone (designated herein as pAX1926) was confirmed by restriction digestion and by DNA sequencing. The manner of construction of pAX1926 is such that the predicted GRG23 translation product contains an amino-terminal extension comprised of MAHHHHHH (residues 1-8 of SEQ IQ NO:36). This N-terminal extension comprises a 'histidine tag' or 'six-His tag' that is useful to facilitate purification of the GRG23 protein, as is well known in the art.

Plasmid pAX1926 containing the grg23 ORF2 has been deposited at the Agricultural Research Service Culture Collection (NRRL) on Nov. 18, 2005, and assigned Accession No. NRRL B-30888.

Example 5 grg23 Confers Resistance to High Levels of Glyphosate

The pUC18-Grg23 construct (pAX1927) was transformed into E. coli strain DH5α and plated out on LB agar plates supplemented with carbenicillin (0.1 mg/mL). Two colonies were selected, resuspended in sterile water, and streaked onto M63 plates containing either 0 mM, 25 mM, 50 mM or 100 mM glyphosate. Isopropyl-B-D-thiogalactopyranoside (IPTG; 0.1 mM) was also added to the plates. As a control, cells containing pUC18 vector alone were transformed and streaked onto glyphosate plates. Following 2 days of growth, these plates were examined for growth (Table 1).

TABLE 1

| Construct | 0 mM glyphosate | 25 mM glyphosate | 50 mM glyphosate | 100 mM glyphosate |
|---|---|---|---|---|
| pUC18 | + | − | − | − |
| pUC18-Grg23 (pAX1927) | + | ++ | ++ | ++ |

This result confirms that expression of grg23 to produce GRG23-ORF2 confers glyphosate resistance in E. coli to at least 100 mM. Additionally, the growth of E. coli containing pAX1927 is stronger in the presence of glyphosate than in the absence of glyphosate.

Example 6

Homology of GRG23 with Other Proteins

The deduced amino acid sequence of GRG23 has homology to EPSPS enzymes, indicating that grg23 encodes an EPSPS.

Examination of the deduced amino acid sequence of GRG-ORF2 (SEQ ID NO:4) reveals that it does not contain the four domains typical of Class II EPSPS enzymes. Thus it is a novel, non-Class II, glyphosate-resistant EPSPS.

Figure 1A:
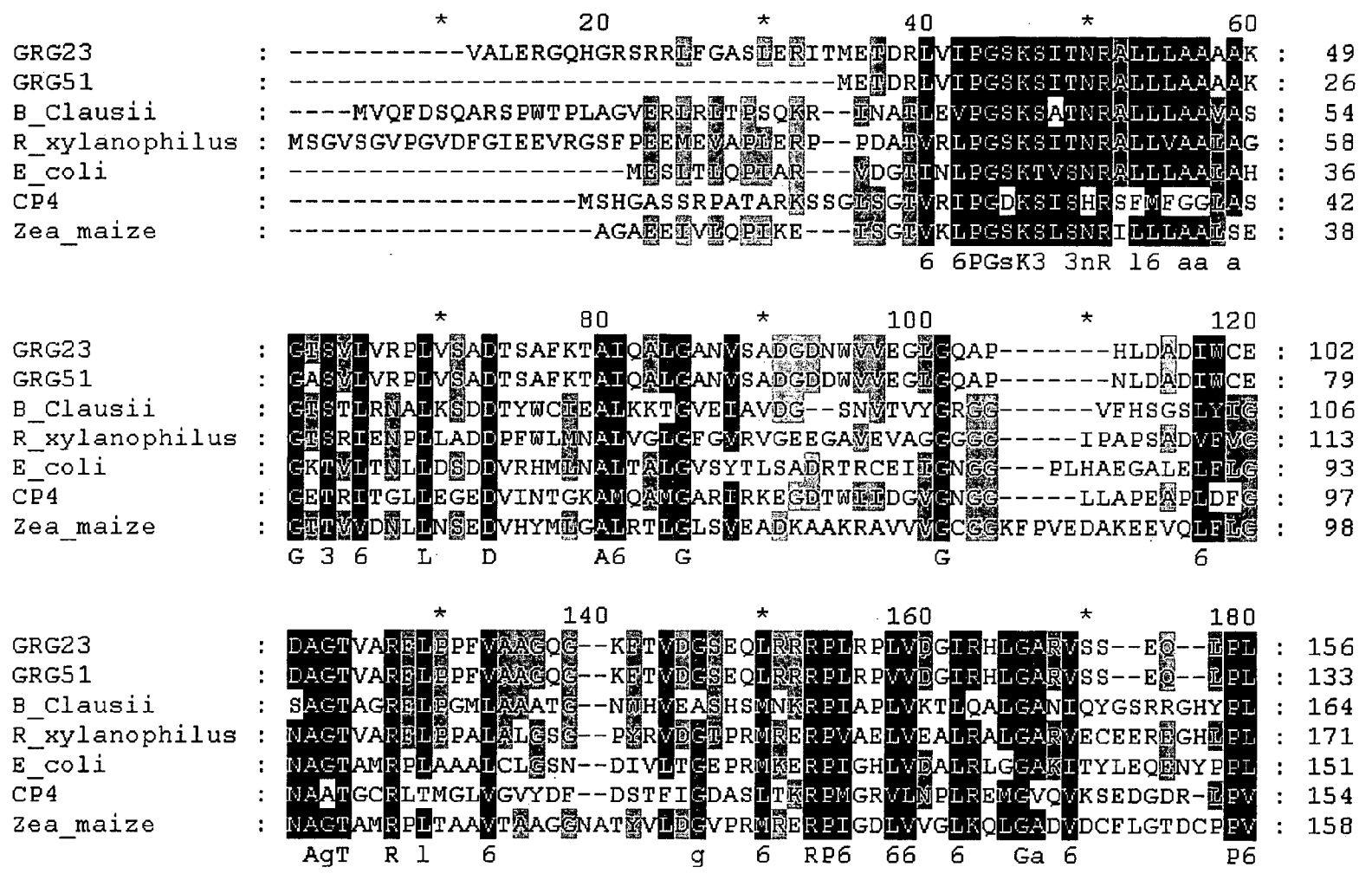
Figure 1B:
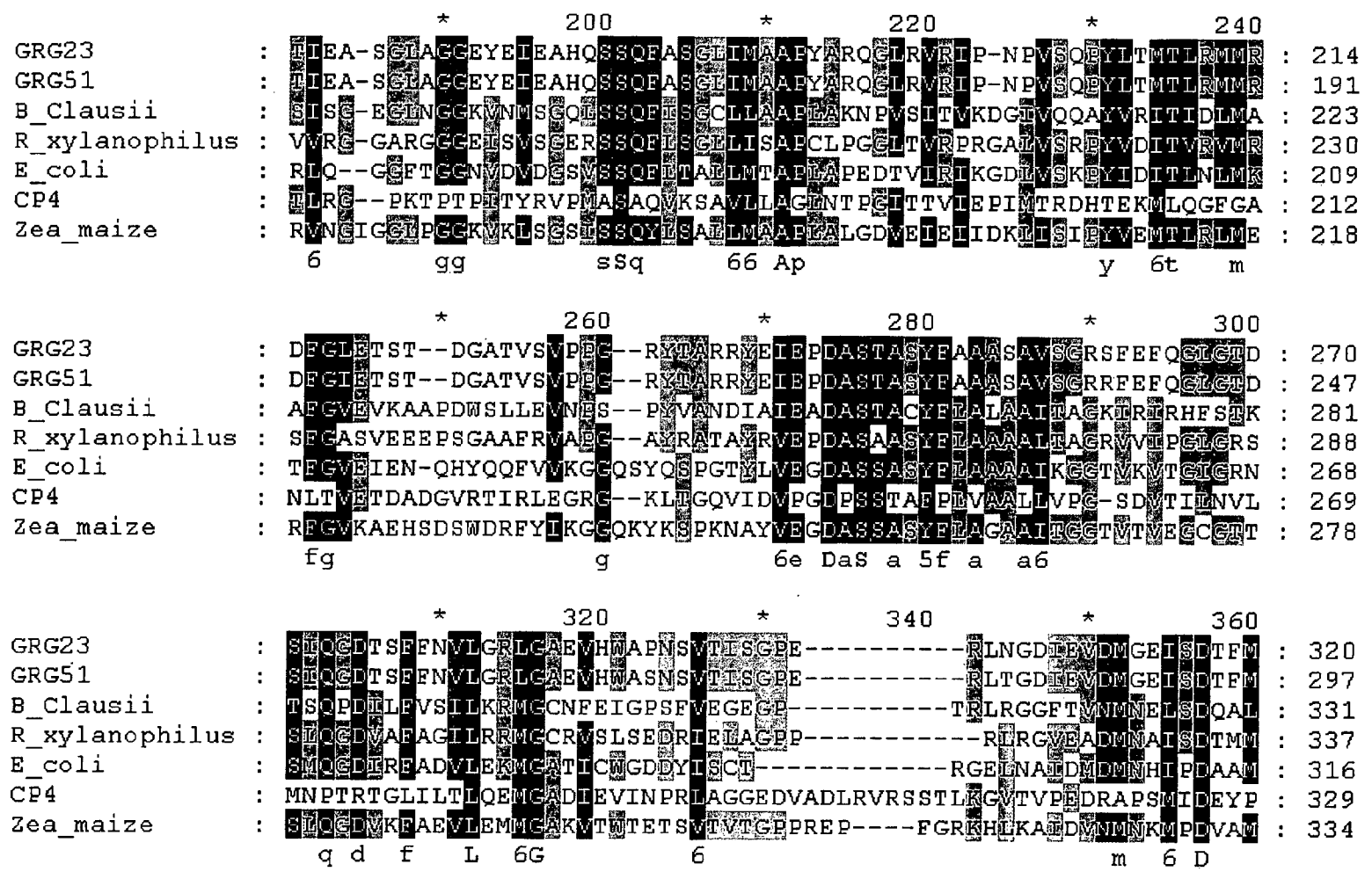

Searching of publicly available protein databases, such as SWISSPROT, reveal that GRG23 has amino acid similarity to the broad class of EPSPS enzymes. However, no protein in any database has greater than 50% identity to the GRG23 amino acid sequence. A representative alignment of GRG23 with other EPSPS enzymes is shown in FIG. 1.

Example 7

Purification of GRG23

The pRSF1b-grg23 construct (pAX1926) was expressed in E. coli following induction with IPTG, and purified in a single step using a cobalt chromatography column as known in the art. Following column elution, purified GRG23 was dialyzed against 50 mM HEPES/100 mM KCl, pH 7.0. The protein was greater than 95% pure as assessed by PAGE. The amount of GRG23 was quantified using the method of Bradford, as is well known in the art (Bradford (1976) Anal. Biochem. 72:248-254).

Example 8

Kinetic Assays of GRG23 Activity

Samples of purified proteins were assayed for EPSPS activity using a kinetic assay involving incubation of PEP (Sigma, St. Louis, Mo.) and S3P in a buffer containing potassium chloride and HEPES at pH 7.0. Liberation of phosphate was detected using a coupled assay for the fluorescent detection of phosphate based on the generation of Amplex Red, as is known in the art (Vazquez et al. (2003) Anal. Biochem. 320: 292-298).

The published assay conditions can lead to saturation of the assay in experiments where phosphate is liberated very quickly. This saturation somewhat limits the dynamic range of the assay, and requires a defined range of enzyme concentrations. It was determined that the kinetic limitation of the fluorescent phosphate assay is apparently due to a combination of factors, including a limitation of inosine and PNP. In the present invention, assay conditions have been developed that yield substantially improved dynamic range and allow the use of a wider range of enzyme and substrate concentrations. The assay conditions that have been significantly changed include the concentrations of purine nucleoside phosphorylase (PNP), xanthine oxidase (XOD), AMPLEX® Red, and inosine, each of which were increased in concentration in the assay to accommodate higher rates of phosphate turnover. This assay was adapted for use to measure EPSPS activity in a 96 well format with the following improvements:

TABLE 2

An improved fluorescence assay

| | Improved Assay | Vazquez et al., 2003 | Units |
|---|---|---|---|
| XOD | 1 | .4 | IU/ml |
| PNP | 2 | .02 | IU/ml |
| Inosine | 2.25 | 1.5 | mM |
| HRP | 1 | 1 | IU/ml |
| Amp Red | 1,100 | 50 | uM |
| Hepes | 26.25 | — | mM |
| KCl | 26.25 | — | mM |
| pH | 7 | 7.4 | |
| Tris | — | 50 | mM |

Enzymatic assays were carried out in 96-well plates in a total volume of 50 uL. Reactions were carried out at room temperature at pH 7.0. All assay components except PEP, EPSPS, and S3P were combined into a Master Mix and aliquoted into a 96-well plate using a multi-channel pipettor. Appropriate PEP concentrations were then added to each well. Fresh dilutions of EPSPS were prepared and added to the appropriate wells. Each assay was initiated by the addition of S3P.

Rate data were plotted and the $K_m$ and $K_{cat}$ kinetic parameters determined by use of the application of the Michaelis-Menten equation using a non-linear curve fit program (KALEIDAGRAPH®, Synergy Software). $K_i$ data were determined by measuring the $K_m$ (app) at multiple glyphosate concentrations, and plotting of $K_m$(app) as a function of inhibitor concentration.

TABLE 3

Effect of Glyphosate on $K_m$ (app) of GRG23

| Glyphosate Concentration (uM) | $K_m$ (app) |
|---|---|
| 0 | 10.95 |
| 3000 | 18.89 |
| 5000 | 20.67 |
| 1000 | 25.23 |

By plotting the $K_m$(app) as a function of glyphosate concentration, a linear representation of the glyphosate resistance of GRG23 can be obtained. The X intercept of the resulting line represents the $-K_i$. Plotting this line with the data shown in Table 3 yields the following data:

TABLE 4

Kinetic values for GRG23

| Enzyme | $K_m$ (μM) | $K_i$ (μM) | Kcat (sec-1) | Ratio of $K_i/K_m$ |
|---|---|---|---|---|
| GRG23 | 10.95 | 9,525 | 8.2 | 869 |

GRG23 is highly resistant to glyphosate, with a $K_i$ of over 9 mM, and a $K_i/K_m$ ration over 800

Example 9

Isolation of ATX21313

For strain ATX 21313, approximately one gram of soil was suspended in 10 ml of water, and 100 μl was used to inoculate a 1 ml culture of mineral salts medium A (MSMA) and no glyphosate. MSMA contains (per 1 liter, pH 7.0) 1 g $NH_4Cl$, 10 g sucrose, 0.2 g $MgSO_4.7H_2O$, 0.01 g $FeSO_4.7H_2O$, 0.007 g $MnSO_4.H_2O$ supplemented with phosphates. After an overnight incubation, the culture was plated onto a solid medium containing MSMA and 50 mM glyphosate, incubated for a few days, and inoculated onto Luria Bertani agar plates to confirm single colony type. Growth in the presence of 50 mM glyphosate was reconfirmed by regrowing on MSMA, 50 mM agar plates. This isolation method yielded strain ATX21313, which was able to grow well under these conditions.

Example 10

Cloning of Glyphosate-Resistant EPSP SYNTHASES

Genomic DNA was extracted from strain ATX21313 and the resulting DNA was partially digested with restriction enzyme Sau3A 1 to yield DNA fragments approximately 5 kilobases in size. These DNA molecules were size selected on agarose gels, purified, and ligated into LAMBDA ZAP® vector arms pre-digested with BamHI. The ligated arms were then packaged into phage particles, and phage titers were determined as known in the art. The resulting libraries were amplified by methods known in the art to generate a library titer of between $3 \times 10^7$ and $3 \times 10^8$ PFU/mL. For each independent library, E. coli (XL1 Blue MRF') was then co-transfected with phage from an amplified library as well as M13 helper phage into to allow mass excision of the library in the form of an infectious, circular ssDNA as known in the art (Short et al. (1988) Nucleic Acids Research 16:7583-7600). After centrifugation of the co-infected cells, the phage-containing supernatant was heated to 65-70° C. for 15-20 minutes to incapacitate any residual lambda phage particles. Dilutions of the resulting ssDNA plasmid library were transfected into a fresh culture of competent E. coli XL1 Blue MRF' cells and also XL-Blue MRF'(ΔaroA) cells (XL1 Blue MRF'). The resulting transfected cells were plated onto M63 plates containing kanamycin, 0.1 mM IPTG and either 0 mM, 20 mM or 50 mM glyphosate. This screening method allows identification of clones containing glyphosate-tolerant EPSP synthases, as well as clones carrying tolerance to glyphosate. Colonies growing on 20 mM or 50 mM glyphosate in the ΔaroA strain or XL-Blue MRF' were picked and their plasmids analyzed by restriction digest to identify plasmids with shared restriction patterns. Individual plasmids were sequenced by methods known in the art, with preference given to plasmids that conferred resistance to 50 mM glyphosate.

Using this approach, as sometimes modified for each library as known and appreciated in the art, library clones containing EPSP synthase genes were identified.

The sequences of the regions of the resulting clones were determined in the region of the EPSP synthase.

Example 11

DNA and Protein Sequences of EPSP Synthases

The DNA sequence of the glyphosate-resistant EPSP synthase was determined for pAX1967 by methods well known in the art. The DNA sequence of grg51 is provided herein as SEQ ID NO:5. The predicted translation product of grg51 (GRG51) is provided herein as SEQ ID NO:6. GRG51 shows 97% amino acid identity to GRG23 (SEQ ID NO:2).

Plasmid pAX1967 containing grg51 has been deposited at the Agricultural Research Service Culture Collection (NRRL) on Jun. 26, 2006, and assigned Accession No. NRRL B-30949.

Table 5 summarizes the homology of GRG23 and GRG51 with other EPSP synthase enzymes.

TABLE 5

Amino acid identity of GRG23-ORF1 and GRG51 to representative EPSPS enzymes

| EPSPS | % Identity to GRG23 | % Identity to GRG51 |
|---|---|---|
| GRG23 | — | 92% |
| GRG51 | 92% | — |
| B_Clausii | 36% | 35% |
| R_xylanophilus | 39% | 38% |
| E_coli | 32% | 32% |
| CP4 | 20% | 21% |
| Zea_maize | 32% | 32% |

Example 12

Cloning of Novel Glyphosate-Resistant EPSP Synthases into an *E. coli* Expression Vector The grg51 gene contained in pAX1967 was sub-cloned into the *E. coli* expression vector pRSF1b (Invitrogen). Resulting clones were confirmed by DNA sequencing, and used to induce expression of grg51 in *E. coli*. The expressed His-tagged protein was then purified as known in the art.

Example 13

Glyphosate Resistance of EPSP Synthases

Cells containing pAX1967 were plated onto M63+ plates containing antibiotic and either 0 mM or 20 mM glyphosate. Growth was scored after two days growth at 37° C. GRG51 was observed to confer resistance to 20 mM glyphosate in *E. coli* cells (Table 6).

TABLE 6

| | Glyphosate screen | |
|---|---|---|
| EPSPS | Plasmid Clone | Growth on 20 mM glyphosate |
| Vector | − | − |
| GRG51 | pAX1967 | ++ |

Example 14 syngrg23 Design and Expression

A novel gene sequence encoding the GRG23 protein (SEQ ID NO:2; U.S. Patent Application No. 60/741,166 filed Dec. 1, 2005) was designed and synthesized. This sequence is provided as SEQ ID NO:12. This open reading frame, designated "syngrg23" herein, was cloned into the expression vector pRSF1b (Invitrogen), by methods known in the art.

The syngrg23 gene encoding GRG23 was cloned into a pUC19 vector to create pAX748. PCR primers that flanked syngrg23 in this vector were used to amplify syngrg23 from pAX748 using the MUTAZYME® II system (Stratagene) to introduce random mutations into the syngrg23coding region. The template was diluted 1:50 in the error-prone PCR reaction, and amplification was carried out for 30 cycles. The resulting PCR product was digested with the restriction enzymes BamH I and Sgs I, gel-purified, and ligated into the vector pRSF1b to create a mutagenized syngrg23 library.

The mutagenized syngrg23 libraries were transformed into *E. coli* strain BL21*DE3 star (Invitrogen). Following transformation, individual colonies were plated on 1× M63 medium containing 150 mM glyphosate to select for clones that had retained enzymatic activity and growth tolerance.

Example 15

Screening for Glyphosate Resistance on Plates

Library ligations were transformed into BL21*DE3 competent *E. coli* cells (Invitrogen). The transformations were performed according to the manufacturer's instructions with the following modifications. After incubation for 1 hour at 37° C. in SOC medium, the cells were sedimented by centrifugation (5 minutes, 1000×g, 4° C.). The cells were washed with 1 ml M63+, centrifuged again, and the supernatant decanted. The cells were washed a second time with 1 ml M63+ and resuspended in 200 ul M63+.

For selection of mutant GRG23 enzymes conferring glyphosate resistance in *E. coli*, the cells were plated onto M63+ agar medium plates containing 150 mM glyphosate, 0.05 mM IPTG (isopropyl-beta-D-thiogalactopyranoside), and 50 ug/ml kanamycin. M63+ medium contains 100 mM $KH_2PO_4$, 15 mM $(NH_4)_2SO_4$, 50 µM $CaCl_2$, 1 µM $FeSO_4$, 50 µM $MgCl_2$, 55 mM glucose, 25 mg/liter L-proline, 10 mg/liter thiamine HCl, sufficient NaOH to adjust the pH to 7.0, and 15 g/liter agar. The plates were incubated for 36 hours at 37° C.

Individual colonies were picked and arrayed into 384-well plates. Two 384-well plates were created in this manner. A third plate of 384 clones was picked from colonies that grown on plates lacking glyphosate.

Example 16

Preparation of Extracts Containing Glyphosate Resistant GRG23 Mutants

BL21*DE3 cells transformed with GRG23 mutants growing on glyphosate plates were grown in LB medium supplemented with 50 ug/ml kanamycin at 37° C. When the culture media reached an optical density (600 nm) of 0.6, 0.5 mM IPTG was added, and the cultures were incubated for 16 hours at 20° C. The cultures were centrifuged at 12,000×g for 15 minutes at 4° C., the supernatant was removed, and the cells were resuspended in 50 mM HEPES/KOH pH 7.0, 300 mM NaCl, 1 mg/ml lysozyme, 0.04 ml DNase I. The resuspended cells were incubated for 1 hour at room temperature. The cells were sonicated 3 times for 10 seconds using a Misonix Sonicator 3000 at setting 7.5. Between sonication bursts the cells were incubated on ice for 30 seconds. The cell lysates were centrifuged at 27000×g for 15 minutes at 4° C., and the supernatant comprising the cell extract was recovered. The cell extracts were dialyzed 2× for 4 hours against 50 mM HEPES/KOH pH 7.0, 300 mM NaCl and stored at 4° C.

Library plates of extracts of mutagenized syngrg23 clones were assayed for improved enzymatic activity as follows: Library clones were pinned into 96-well blocks containing LB medium and were grown to an O.D. of about 0.6. IPTG was then added (0.5 mM) and the blocks were incubated overnight at 20° C. to induce protein expression. Protein extracts were prepared from the cell pellets using POP culture reagent (Novagen), and the enzymatic activity in the crude lysates was measured. Extracts with activity equal to or superior to GRG23 were selected for further analysis. The DNA sequences of the clones corresponding to these extracts were determined. Table 7 shows the amino acid changes identified in six variants of GRG23 that retained glyphosate resistance: grg23(L3P1.B20) (SEQ ID NO:26) encoding the amino acid sequence GRG23(L3P1.B20) (SEQ ID NO:27); grg23 (L3P1.B3) (SEQ ID NO:28) encoding the amino acid sequence GRG23(L3P1.B3) (SEQ ID NO:29); grg23 (L3P1.F18) (SEQ ID NO:30) encoding the amino acid sequence GRG23(L3P1.F18) (SEQ ID NO:31); and grg23 (L3P1.O23) SEQ ID NO:31, encoding the amino acid sequence GRG23(L3P1.O23) SEQ ID NO:32).

TABLE 7

Mutations identified in glyphosate-resistant GRG23 variants

| Clone | Amino Acid (AA) in GRG23 |
|---|---|
| L3P1B20 | V206→I |
| L3P1B3 | D75→H, E217→K |
| L3P1F18 | T274→I |
| L3P1O23 | R5→H |

Each of the clones were re-grown in 250 mL LB cultures, and protein expression induced with IPTG. Following induction, the mutant GRG23 protein was purified from each culture by affinity chromatography using a cobalt resin (Novagen). The purified proteins were then tested for enzymatic activity following heating for 0, 2 and 4 hours at 37° C. One of the clones, termed "M5", was found to retain an increased proportion of its enzymatic activity after prolonged incubation at 37° C. (Table 8). The DNA sequence of this clone was determined, and the gene is designated herein as grg23(ace1) (SEQ ID NO: 14). The protein expressed from grg23(ace1) is designated GRG23(ACE1) (SEQ ID NO:15).

TABLE 8

Half-life of GRG23(ACE1) vs GRG23 at elevated temperature

| Protein | Half-life at 37° C. (hours) |
|---|---|
| GRG23 | 7 |
| GRG23(ACE1) | 15.5 |

GRG23(ACE1) contains 2 amino acid substitutions relative to wild-type GRG23 protein: A49→T and S276→T. The pRSF1b vector that contains this gene is designated pAX3801.

Example 17

Quantification of Extracts Containing Glyphosate Resistant GRG23 Mutants

The expression of GRG23 variant proteins in cell extracts was determined by a quantitative antibody dot blot. Two sheets of 3 mM filter paper were soaked in 1×PBS buffer (20 mM potassium phosphate pH 7.2, 150 mM NaCl) and placed in a 96 well dot blot manifold (Schleicher and Schuell, Keene, N.H.). One sheet of Optitran BA-S 83 cellulosenitrate membrane (Schleicher and Schuell) was soaked in 1×PBS buffer and placed on top of the 3 mM filter paper. Serial dilutions of cell extracts as well as dilutions of purified GRG-1 wild-type protein of known concentration ("protein standards") were prepared in a final volume of 100 ul 1×PBS. The samples were loaded into the dot blot wells and a vacuum of 10 cm Hg was applied. The wells were washed 3× times with 300 ul PBS. The cellulose nitrate membrane was removed and blocked for one hour in 3% dry milk in PBS. The blocking solution was removed and the cellulose nitrate membrane was incubated with an anti-6×His monoclonal antibody conjugated to horseradish peroxidase (Serotec, Raleigh, N.C.) diluted 1:5000 in 3% dry milk in PBS. After one hour incubation at room temperature, the membrane was washed four times for five minutes with PBS-T (0.05% Tween20 in PBS). The membrane was incubated with ECL PLUS™ western blotting detection reagent (Amersham Biosciences, Piscataway, N.J.) for five minutes at room temperature. The detection solution was removed and a Biomax Light film (Kodak) was placed on top of the membrane and exposed for ten minutes. The film was scanned and signal quantitation was performed using Phoretix Array software (Nonlinear Dynamics, Durham, N.C.) by comparison to the GRG23 protein standards.

Example 18

Determination of EPSPS Activity of GRG-23 Variants

Extracts containing GRG23 variant proteins were assayed for EPSP synthase activity as described above. Assays were carried out in a final volume of 50 ul containing 0.5 mM shikimate-3-phosphate, 0-500 uM phosphoenolpyruvate (PEP), 1 U/ml xanthine oxidase, 2 U/ml nucleoside phosphorylase, 2.25 mM inosine, 1 U/ml horseradish peroxidase, 0-2 mM glyphosate, 50 mM HEPES/KOH pH 7.0, 300 mM NaCl, and AMPLEX® Red (Invitrogen) according to the manufacturer's instructions. Extracts were incubated with all assay components except shikimate-3-phosphate and AMPLEX®Red for 5 minutes at room temperature, and assays were started by adding shikimate-3-phosphate and AMPLEX® Red. EPSP synthase activity was measured using a Spectramax Gemini XPS fluorescence spectrometer (Molecular Dynamics, excitation: 555 nm; emission: 590 nm).

Following full determination of kinetic parameters, the kinetic constants were determined as follows, adjusting for the quantity of protein determined by antibody dot-blot analysis. For any one glyphosate concentration, EPSP synthase activity was measured as a function of a broad range of PEP concentrations. The data were fit to the Michaelis-Menten equation using KALEIDAGRAPH® software (Synergy Software) and used to determine the $K_m$ ($K_m$ apparent) of the EPSP synthase at that glyphosate concentration. $K_m$ apparent values were determined at no fewer than 3 glyphosate concentrations, and the $K_i$ of the EPSPS for glyphosate were calculated from the plot of $K_m$ apparent vs. glyphosate concentration, using the equation (m1*x/(m2+x); m1=1; m2==1) as known in the art.

TABLE 9

Kinetics of GRG23(ACE1) vs GRG23

| | Km (uM) | Ki (uM) | Vmax (nmol/min/ug) |
|---|---|---|---|
| GRG23 | 12.2 | 13,800 | 14.77 |
| GRG23(ACE1) | 9.7 | 14,620 | 13.73 |

Example 19

Identification of grg23 (ace2)

GRG23(ACE1) contains two amino acid changes relative to GRG23. To determine if additional substitutions at these positions could further improve activity, a DNA library was generated that resulted in clones expressing proteins that were substantially mutated and both positions 49 and 276 of GRG23. Clones conferring glyphosate resistance were selected by growth on glyphosate plates, and grown and assayed for kinetic properties as described.

Surprisingly, one clone, herein designated grg23(ace2) (SEQ ID NO: 16), encoding the GRG23(ACE2) protein (SEQ ID NO: 17) was identified as having improved thermostability. The DNA sequence of grg23(ace2) shows that GRG23 (ACE2) contains a single amino acid change (residue 276 of GRG23 to arginine).

Example 20

Comparison of GRG23 and GRG51, and Mutagenesis of Differing Residues

Two libraries were generated to assess the permutations of amino acid sequences possible from comparison of the amino acid sequences of GRG23 and GRG51. The first library introduced variation from the GRG51 amino acid sequence into a grg23(ace2) coding region. The second library introduced the variation from GRG23(ACE2) amino acid sequence into the grg51 coding region.

Clones of the resulting libraries were assessed for (1) ability to confer glyphosate resistance upon on a cell, and (2) activity after prolonged incubation at 37° C. A total of ten clones were sequenced and analyzed in more detail. One particular clone, herein designated grg51.4 (SEQ ID NO:18), encoding the protein GRG51.4 (SEQ ID NO:19), contains several amino acid changes relative to both GRG23(ACE2) and GRG51. The amino acid changes present in GRG51.4 relative to GRG23(ACE2) were subsequently introduced into the grg23(ace2) gene, to yield grg23(ace3) (SEQ ID NO:20), which encodes the GRG23(ACE3) protein (SEQ ID NO:21). GRG23(ACE3) exhibits superior activity and thermostability relative to GRG23, and GRG23(ACE2).

GRG23(ace1) was mutagenized, and clones were tested to identify clones expressing variants with improved thermostability and/or activity. One clone, grg23(L5P2.J2) (SEQ ID NO:22), encoding GRG23(L5P2.J2) (SEQ ID NO:23), was identified by virtue of its improved kinetic properties. GRG23 (L5P2.J2) contains three amino acid changes relative to GRG23 (ACE1), as shown in the following Table 10.

TABLE 10

Amino Acid changes in GRG23(L5P2.J2)

| Amino Acid (AA) in GRG23(L5P2.J2) relative to GRG23(ACE1) |
|---|
| V101→F |
| A213→S |
| D284→N |

Oligonucleotide mutagenesis was used to create clones that contain each of the amino acid changes identified GRG23 (L5P2.J2) into the grg23(ace3) coding region. A clone was identified as encoding a protein having improved kinetic properties over GRG23(ACE3), and designated grg23(ace4) (SEQ ID NO:24). The protein encoded by grg23(ace4) is designated as GRG23(ACE4) (SEQ ID NO:25) contains a single amino acid change relative to GRG23(ACE3) (Valine 101 to phenylalanine). Based on this result, a separate oligonucleotide mutagenesis was performed to test the kinetics of each possible amino acid substitutions at position 101. None of the amino acid changes resulted in further improvement in kinetic properties compared to GRG23(ACE4).

TABLE 11

Kinetics of improved variants

| | Km (uM) | Ki (uM) | Vmax (nmol/min/ug) |
|---|---|---|---|
| GRG23 | 14 | 10,800 | 13 |
| GRG51 | 15 | 21,048 | 13 |
| GRG23(ACE1) | 10 | 14,620 | 14 |
| GRG23(ACE2) | 11 | 18,104 | 15 |
| GRG51.4 | 19 | 26,610 | 17 |
| GRG23(ACE3) | 15 | 20,000 | 17 |
| GRG23(L5P2.J2) | 15 | 2,500 | 23 |
| GRG23(ACE4) | 14 | 5,010 | 24 |

Example 21

Engineering grg23 or grg5 for Plant Transformation

The grg23 or grg51 open reading frame (ORF) is amplified by PCR from a full-length cDNA template. Hind III restriction sites are added to each end of the ORF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced using techniques well known in the art to ensure that no mutations are introduced during PCR.

The plasmid containing the grg23 or grg51 PCR product is digested with Hind III and the fragment containing the intact ORF is isolated. This fragment is cloned into the Hind III site of plasmid pAX200, a plant expression vector containing the rice actin promoter (McElroy et al. (1991) *Molec. Gen. Genet.* 231:150-160) and the PinII terminator (An et al. (1989) *The Plant Cell* 1: 115-122). The promoter—gene—terminator fragment from this intermediate plasmid is subcloned into plasmid pSB11 (Japan Tobacco, Inc.) to form a final plasmid, for example, pSB11GRG23. pSB11GRG23 is organized such that the 3.91 kb DNA fragment containing the promoter—grg23—terminator construct may be excised by double digestion with Kpn I and Pme I and used for transformation into plants by aerosol beam injection. The structure of pSB11GRG23 is verified by restriction digest and gel electrophoresis, and by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plating on media containing spectinomycin. Plasmid pSB11GRG23 carries spectinomycin resistance but is a narrow host range plasmid and cannot replicate in *Agrobacterium*. Spectinomycin resistant colonies arise when pSB11GRG23 integrates into the broad host range plasmid pSB1 through homologous recombination. The cointegrate product of pSB1 and pSB11GRG23 is verified by Southern hybridization. The *Agrobacterium* strain harboring the cointegrate is used to transform maize by the PureIntro method (Japan Tobacco).

Example 22

Transformation of grg23 or grg51 into Plant Cells

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express GRG23 in plant cells are accelerated into plant tissue using an aerosol beam accelerator, using conditions essentially as described in PCT Publication No. WO/0138514. After beaming, embryos are incubated for 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media for 5 days at 25° C. in the dark, then transferred to a selection media. Explants are incubated in selection media for up to eight weeks, depending on the nature and characteristics of the particular selection utilized. After the selection period, the resulting callus is transferred to embryo maturation media until the formation of mature somatic embryos is observed. The resulting mature somatic embryos are then placed under low light and the process of regeneration is initiated by methods known in the art. The resulting shoots are allowed to root on rooting media, and the resulting plants are transferred to nursery pots and propagated as transgenic plants.

| Materials DN62A5S Media | | |
|---|---|---|
| Components | per liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 23

Transformation of grg23 or grg51 into Maize Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule selected from the group consisting of:
   a) a nucleic acid molecule comprising the nucleotide sequence of SEQ ID NO:1, 3, or 5, or a complement thereof;
   b) the herbicide resistance nucleotide sequence of the DNA insert of the plasmid deposited as Accession No. NRRL B-30888 or B-30949, or a complement thereof;
   c) a nucleic acid molecule which encodes a polypeptide comprising the amino acid sequence of SEQ ID NO:2, 4, or 6; and,
   d) a nucleic acid molecule comprising a nucleotide sequence encoding a 5-enolpyruvylshikimate-3-phosphate synthase (EPSPS) polypeptide having glyphosate tolerance and having at least 95% amino acid sequence identity to the amino acid sequence of SEQ ID NO:2, 4, or 6.

2. The isolated nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the vector of claim 3.

6. The host cell of claim 5 that is a bacterial host cell.

7. The host cell of claim 5 that is a plant cell.

8. A transgenic plant comprising the host cell of claim 7.

9. The plant of claim 8, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

10. A transformed seed of the plant of claim 8.

11. A method for conferring resistance to glyphosate in a plant, said method comprising transforming said plant with a DNA construct, said construct comprising a promoter that drives expression in a plant cell operably linked with a nucleotide sequence encoding an EPSPS polypeptide having glyphosate tolerance and at least 95 % sequence identity to the amino acid sequence of SEQ ID NO:2, 4, or 6 and regenerating a transformed plant.

12. A plant having stably incorporated into its genome a DNA construct comprising a nucleotide sequence that encodes a protein having herbicide resistance activity, wherein said nucleotide sequence is selected from the group consisting of:
   a) the nucleotide sequence of SEQ ID NO:1, 3, or 5;
   b) a nucleotide sequence encoding a polypeptide comprising the amino acid sequence of SEQ ID NO:2, 4, or 6;
   c) a nucleotide sequence encoding a EPSPS polypeptide having glyphosate tolerance and having at least 95% amino acid sequence identity to the amino acid sequence of SEQ ID NO:2, 4, or 6; and,
   d) the herbicide resistance nucleotide sequence of the DNA insert of the plasmid deposited as Accession No. NRRL B-30888 or NRRL B-30949;
   wherein said nucleotide sequence is operably linked to a promoter that drives expression of a coding sequence in a plant cell.

13. The plant of claim 12, wherein said plant is a plant cell.

* * * * *